United States Patent
Madrid et al.

(10) Patent No.: US 10,882,020 B1
(45) Date of Patent: Jan. 5, 2021

(54) TOPOLOGICALLY SEGREGATED POLYMER BEADS AND METHODS THEREOF

(71) Applicant: SRI International, Menlo Park, CA (US)

(72) Inventors: Peter Madrid, Sunnyvale, CA (US); Pauline Bourbon, San Francisco, CA (US); Michal Avital-Shmilovici, Sunnyvale, CA (US); Nathan Collins, San Mateo, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 15/498,145

(22) Filed: Apr. 26, 2017

Related U.S. Application Data

(60) Provisional application No. 62/327,923, filed on Apr. 26, 2016.

(51) Int. Cl.
| | |
|---|---|
| *C40B 50/00* | (2006.01) |
| *C40B 50/18* | (2006.01) |
| *B01J 19/00* | (2006.01) |
| *C12Q 1/6876* | (2018.01) |
| *C12Q 1/68* | (2018.01) |

(52) U.S. Cl.
CPC ........ *B01J 19/0046* (2013.01); *C12Q 1/6876* (2013.01); *B01J 2219/0061* (2013.01); *B01J 2219/00596* (2013.01); *B01J 2219/00722* (2013.01)

(58) Field of Classification Search
CPC ......... C40B 40/02; C40B 40/00; C40B 30/00; C12Q 1/68
See application file for complete search history.

(56) References Cited

U.S. PATENT DOCUMENTS

| | | | | |
|---|---|---|---|---|
| 5,840,485 | A * | 11/1998 | Lebl | C07K 1/047 506/3 |
| 5,859,191 | A * | 1/1999 | Miller | C07K 5/06078 435/7.1 |
| 2006/0134697 | A1* | 6/2006 | Lam | C07K 1/047 435/7.1 |
| 2010/0222546 | A1* | 9/2010 | Crich | C07K 1/02 530/322 |

OTHER PUBLICATIONS

Fukuyama et al., 1,4-Dinitrobenzenesulfonamides: A Simple and Practical Method for the Preparation of a Variety of Secondary Amines and Diamines, Tetrahedron Letters, 1997, 38(33), 5831-5834. (Year: 1997).*
Rapp, W., Macro Beads as Microreactors: New Solid-Phase Synthesis Methology, Chapter 4, Combinatorial Chemistry: Synthesis and Application, Wilson and Czarnik eds., 1997, 74. (Year: 1997).*
Isidro-Llobet et al., Amino Acid-Protecting Groups, Chem. Rev., 2009, 109, 2455-2504. (Year: 2009).*
Lam, K. S. et al. A new type of synthetic peptide library for identifying ligand-binding activity. Nature 354, 82-84 (1991).
Lam, K. S., Lebl, M. & Krchnák, V. The 'One-Bead-One-Compound' Combinatorial Library Method. Chem. Rev. 97, 411-448 (1997).
Edman, P. Method for determination of the amino acid sequence in peptides. Acta Chem. Scand. 4, 283-293 (1950).
Chait, B. T., Wang, R., Beavis, R. C. & Kent, S. B. Protein ladder sequencing. Science (80). 262, 89-92 (1993). Abstract Only.
Geysen, H. M. et al. Isotope or mass encoding of combinatorial libraries. Chem. Biol. 3, 679-688 (1996).
Barnes, C. & Balasubramanian, S. Recent developments in the encoding and deconvolution of combinatorial libraries. Curr. Opin. Chem. Biol. 4, 346-350 (2000). Abstract Only.
Liu, R., Marik, J. & Lam, K. S. A novel peptide-based encoding system for 'one-bead one-compound' peptidomimetic and small molecule combinatorial libraries. J. Am. Chem. Soc. 124, 7678-7680 (2002). Abstract Only.
Trinh, T. B., Upadhyaya, P., Qian, Z. & Pei, D. Discovery of a Direct Ras Inhibitor by Screening a Combinatorial Library of Cell-Permeable Bicyclic Peptides. ACS Comb. Sci. 18, 75-85 (2016).
Lian, W., Jiang, B., Qian, Z. & Pei, D. Cell-Permeable Bicyclic Peptide Inhibitors against Intracellular Proteins. J. Am. Chem. Soc 2-5 (2014).
Yao, N. et al. Discovery of Targeting Ligands for Breast Cancer Cells Using the One-Bead One-Compound Combinatorial Method. J. Med. 52, 126-133 (2009).
Debenham, S. D., Snyder, P. W. & Toone, E. J. Solid-phase synthesis for the identification of high-affinity bivalent lectin ligands. J. Org. Chem. 68, 5805-5811 (2003). Abstract Only.
Vágner, J. et al. Enzyme-mediated spatial segregation on individual polymeric support beads: application to generation and screening of encoded combinatorial libraries. Proc. Natl. Acad. Sci. U. S. A. 93, 8194-8199 (1996).
Bujacz, A. Structures of bovine, equine and leporine serum albumin. Acta Cryst. D68, 1278-1289 (2012). Abstract Only.
Han, J. C. & Han, G. Y. A Procedure for Quantitative Determination of Tris(2-Carboxyethyl)phosphine, an Odorless Reducing Agent More Stable and Effective Than Dithiothreitol. Anal. Biochem. 220, 5-10 (1994). Abstract Only.

(Continued)

*Primary Examiner* — Amy M Bunker
(74) *Attorney, Agent, or Firm* — Dicke, Billig & Czaja PLLC

(57) ABSTRACT

Embodiments in accordance with the present disclosure are directed to polymer beads and uses thereof, including forming libraries of compounds for screening and assay purposes. A polymer bead, in accordance with embodiments, has an interior surface and an exterior surface that are topologically segregated from one another. The interior surface includes a protecting group and the exterior surface includes a deprotected group, which can also be referred to as a deprotected functional group. The protecting group can includes a nitrobenzenesulfonamide group that protects an amine group.

9 Claims, 28 Drawing Sheets

(13 of 28 Drawing Sheet(s) Filed in Color)

(56) References Cited

OTHER PUBLICATIONS

Burns, J. A., Butler, J. C., Moran, J. & Whitesides, G. M. Selective Reduction of Disulfides by Tris(2-carboxyethyl)phosphine. J. Org. Chem 56, 2648-2650 (1991). tumor marker for patients with mesothelioma and ovarian cancer. Clin Cancer Res 12(2)447-53.y.

Kan, T. & Fukuyama, T. Ns strategies: a highly versatile synthetic method for amines. Chem. Commun. 353-359 (2004). doi:10.1039/b311203a. Abstract Only.

Smith, J. M., Moreno, J., Boal, B. W. & Garg, N. K. Total synthesis of the akuammiline alkaloid picrinine. J. Am. Chem. Soc. 136, 4504-4507 (2014).

Ngu, K., Patel, D. V & Francisco, S. S. Preparation of Acid-labile Resins with Halide Linkers and their Utility in Solid Phase Organic Synthesis. Tetrahedron Lett. 38, 973-976 (1997). Abstract Only.

Patgiri, A., Menzenski, M. Z., Mahon, A. B. & Arora, P. S. Solid-phase synthesis of short '-helices stabilized by the hydrogen bond surrogate approach. Nat. Protoc. 5, 1857-1865 (2010).

Fukuyama, T., Cheung, M., Jow, C. K., Hidai, Y. & Kan, T. 2,4-Dinitrobenzenesulfonamides: A simple and practical method for the preparation of a variety of secondary amines and diamines. Tetrahedron Lett. 38, 5831-5834 (1997). Abstract Only.

Carrotta, R. et al. Protein stability modulated by a conformational effector: effects of trifluoroethanol on bovine serum albumin. Phys. Chem. Chem. Phys. 11, 4007-4018 (2009).

Roccatano, D., Colombo, G., Fioroni, M. & Mark, A. E. Mechanism by which 2,2,2-trifluoroethanol/water mixtures stabilize secondary-structure formation in peptides: a molecular dynamics study. Proc. Natl. Acad. Sci. U. S. A. 99, 12179-12184 (2002).

Povey, J. F., Smales, C. M., Hassard, S. J. & Howard, M. J. Comparison of the effects of 2,2,2-trifluoroethanol on peptide and protein structure and function. J. Struct. Biol. 157, 329-338 (2007).

Sönnichsen, F. D., Van Eyk, J. E., Hodges, R. S. & Sykes, B. D. Effect of trifluoroethanol on protein secondary structure: an NMR and CD study using a synthetic actin peptide. Biochemistry 31, 8790-8798 (1992). Abstract Only.

McAlpine, S. R. & Schreiber, S. L. Visualizing Functional Group Distribution in Solid-Support Beads by Using Optical Analysis. Chem.—A Eur. J. 5, 3528-3532 (1999). Abstract Only.

Luisa, M. et al. Solid-Phase Synthesis of N-Nosyl-and N-Fmoc-N-Methyl-r-amino Acid. J. Org. Chem 3723-3728 (2007). Copy Unavailable.

Hsieh HB, Marrinucci D, Bethel K, et al., "High speed detection of circulating tumor cells", Biosensors and Bioelectronics, 2006; 21: 1893-1899. Abstract Only.

Krivacic RT, Ladanyi A, Curry DN, et al., "A rare-cell detector for cancer", Proc Natl Acad Sci USA, 2004;101: 10501-10504.

* cited by examiner

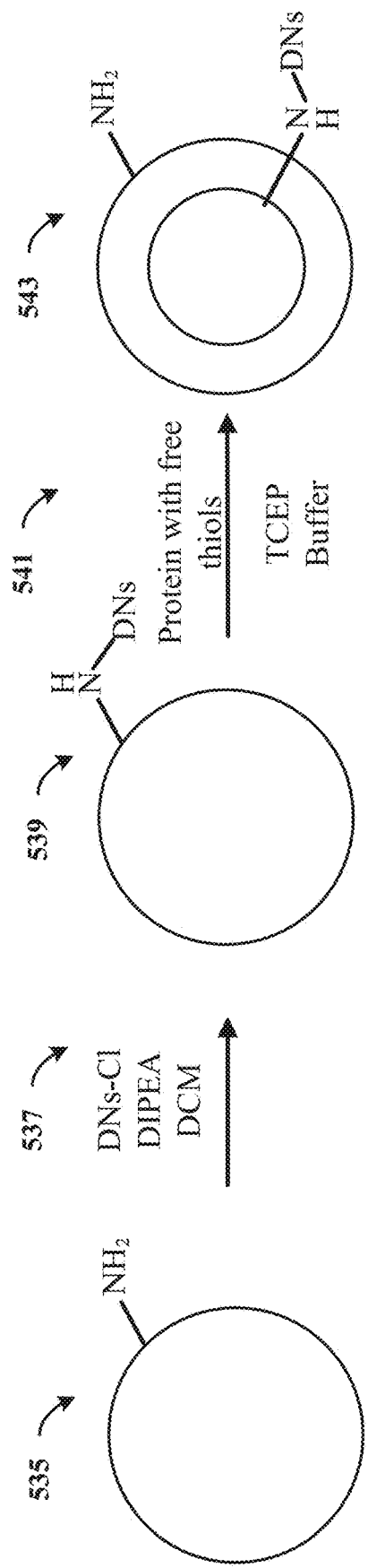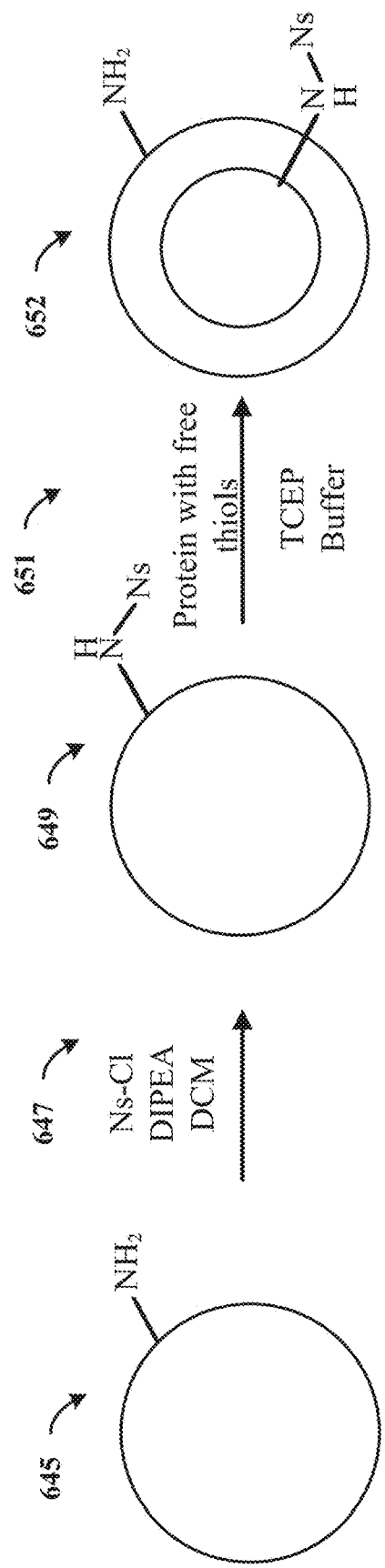

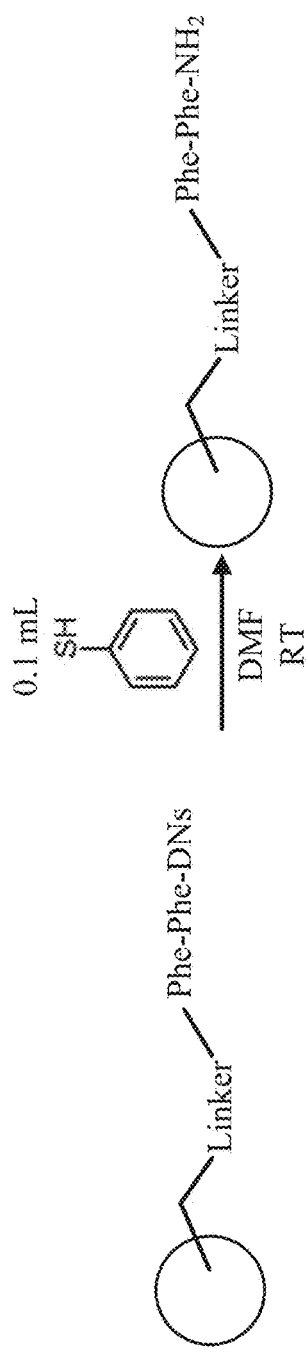
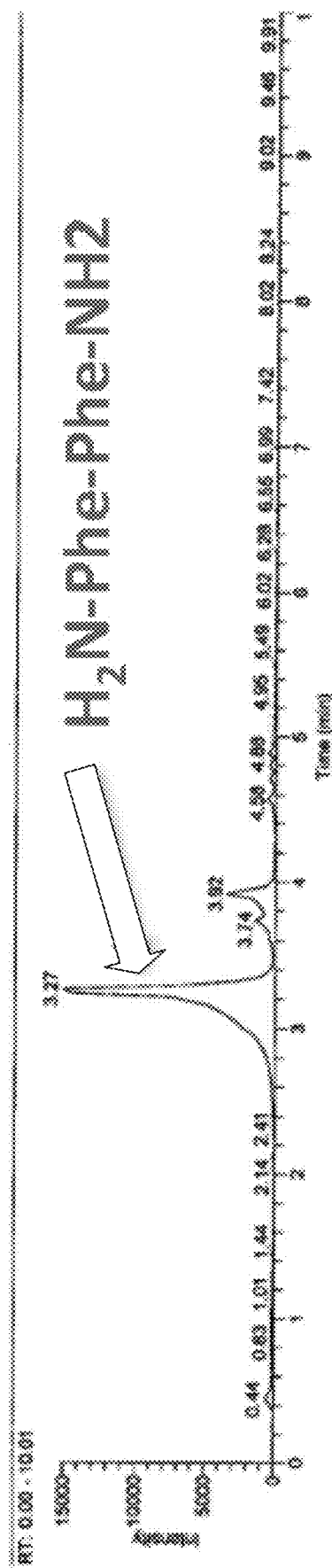
FIG. 13A
FIG. 13B

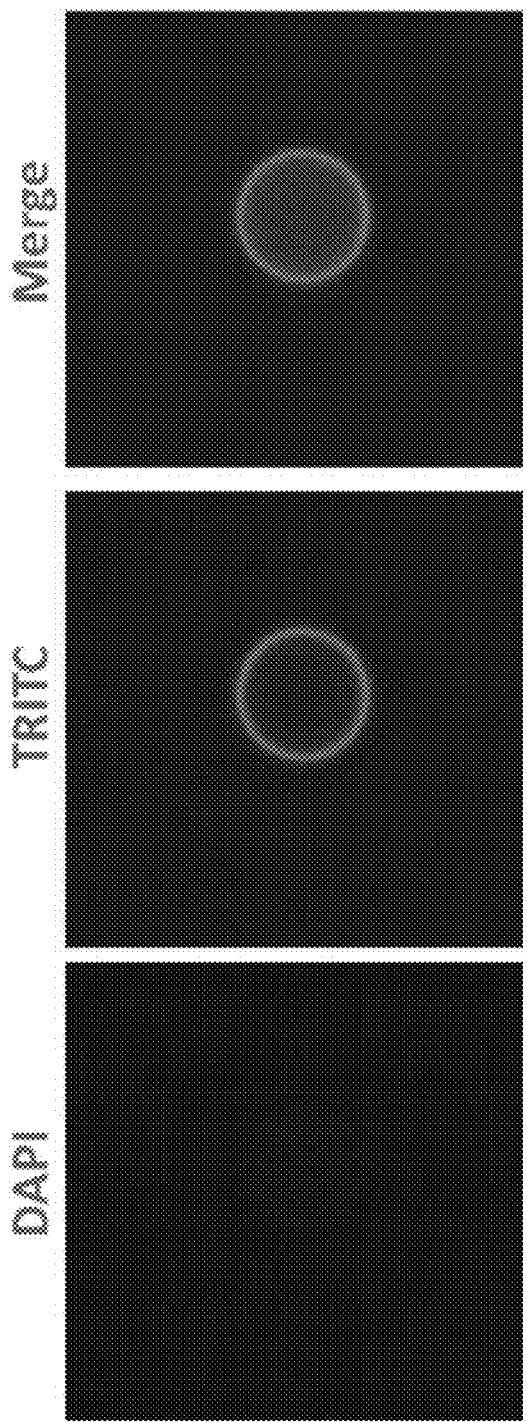
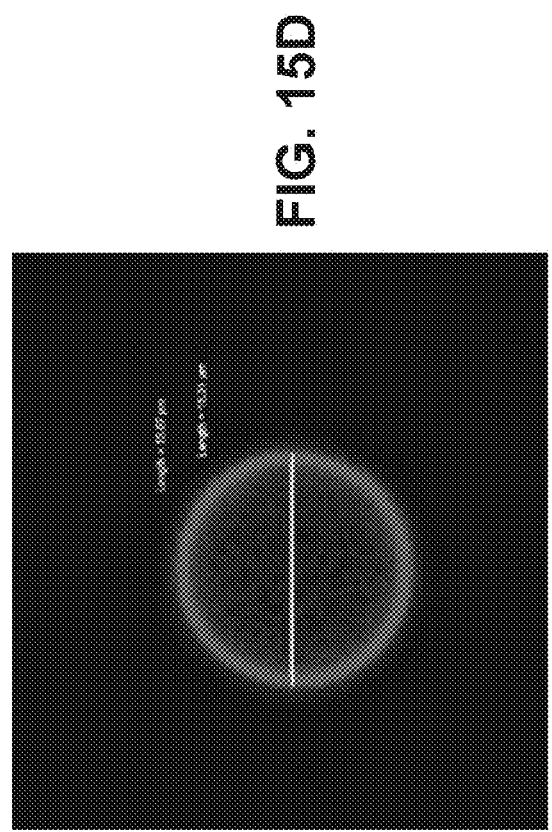
FIG. 15A
FIG. 15B
FIG. 15C
FIG. 15D

TOPOLOGICALLY SEGREGATED POLYMER BEADS AND METHODS THEREOF

FEDERALLY-SPONSORED RESEARCH AND DEVELOPMENT

This invention was made with the support of the Defense Advanced Research Projects Agency (DARPA) and SPAWAR Systems Center Pacific (SSC Pacific) under Contract No. N66001-14-C-4059. The U.S. Government has certain rights in this invention.

OVERVIEW

Polymer beads can be used to form libraries of compounds, such as naturally or synthetically produced oligomers or polymers (e.g., peptides, non-peptides and small molecules). In some instances, the concept of "one-bead one-compound" (OBOC) combinatorial libraries can be used to generate the different compounds. The library can be used to screen for compounds that react to a target or provide a particular function. The OBOC library can include the use of a split synthesis approach and ultimately each bead has only one chemical entity. Using such an approach, libraries of compounds can be synthesized and screened for hits, such as a hit of compound for particular purposes (e.g., binding to a target). Structural determination of a screened compound can be performed by Edman chemistry, ladder sequencing, or isotope encoding. The structural determination techniques can have limitations, such as the coding can interfere with the binding assay. In various implementations, libraries are generated on 90 μm beads, which can limit the number of beads that can be screened on a plate. Various applications, such as screening or diagnostic assays, can benefit from screening of large numbers of compounds, such as 10^8 to 10^9 compounds.

SUMMARY OF THE INVENTION

The present invention is directed to overcoming the above-mentioned challenges and others related to forming and screening libraries of compounds for particular purposes. Specific aspects are directed to polymer beads that are topologically segregated to include a protecting group in the interior surface and a deprotected group in the exterior surface. Such beads can be used to form a library of greater than 10^8 screening compounds that can be screened using the different encoding compounds in the interior surface. In specific aspects, the library formed can be used to screen a plate of five million beads. For example, a compound of interest, e.g., the screening compound, can be present in the exterior surface of the bead and an encoding compound can reside in the interior surface of the bead. The present invention is exemplified in a number of implementations and applications, some of which are summarized below as examples.

In specific aspects, a protein with free cysteines can be used to topologically segregate a polymer bead. The polymer bead can have an interior surface and an exterior surface that are topologically segregated with respect to one another. The polymer bead is porous and/or hollow, e.g., has a hollow cavity that is defined by the interior surface. The free cysteines of the protein can selectively deprotect amine groups in the exterior surface without deprotecting amine groups in the interior surface of the bead. In some aspects, the protein is Bovine Serum Albumin (BSA) which is a globular protein containing seventeen disulfide bonds. BSA has a molecular weight of 66.5 kilodalton (kDa) and may not penetrate into the polymer bead. Further, the disulfide bonds of BSA can be reduced to the corresponding thiol with the use of tris(2-carboxyethyl)phosphine (TCEP). Nitrobenzenesulfonamides can be used as a protecting group, sometimes referred to as an "activating group", in both liquid or solid phase synthesis. Nitrobenzenesulfonamides can be deprotected using thiols. Specifically, a polymer bead can be reacted with a nitrobenzenesulfonamides protecting group such that the protecting group is present on the interior and exterior surfaces of the polymer bead. The polymer bead is then reacted with the protein (e.g., BSA reacted with TCEP) resulting in the interior surface including the protecting group and the exterior surface including a deprotected group (e.g., a functional group that is not protected, which can be also referred to as a "deprotected functional group").

Various embodiments of the present disclosure are directed to a polymer bead having an interior surface and an exterior surface that are topologically segregated with respect to one another. The interior surface includes a first protecting group, such as a nitrobenzenesulfonamide group. The exterior surface includes a first deprotected group, such as an amine group (e.g., $NH_2$, sometimes referred to as a primary amine). The polymer bead can have a diameter in a range of (less than) 90 microns and 10 microns. In specific aspects, the polymer bead is a 10 micron Tentagel bead. The first protecting group can be 2-4-Dinitrobenzenesulfonamide (DNs) or 2-nitrobenzenesulfonamide (Ns), although embodiments are not so limited. The first protecting group can protect a protected group (e.g., a functional group that is protected, which can also be referred to as a "protected functional group"), such as an amine group (e.g., NH coupled to the protecting group) in the interior surface. In specific aspects, the first deprotected group in the exterior surface can be coupled to a screening compound. Alternatively and/or in addition, the protected group in the interior surface can be deprotected and coupled to an encoding compound used to label the screening compound.

In some specific alternative embodiments, the topologically segregated polymer bead includes a screening compound in the exterior surface and the encoding compound in the interior surface. The topologically segregated bead can have surface-functionalized groups used to build the screening compound and encoding compound. The screening compound can be coupled to a first functional group (e.g., an amine group) in the exterior surface and the encoding compound can be coupled to a second functional group (e.g., another amine group) in the interior surface in a controlled manner using additional protecting groups (e.g., a second protecting group, such as fluorenylmethyloxycarbonyl chloride (Fmoc), and a third protecting group, such as tert-butyloxycarbonyl (Boc)). For instance, the additional protecting groups can selectively deprotect using an acid and a base. Beads, in some specific aspects, can thereby include a polymer bead having an interior surface and an exterior surface that are topologically segregated from one another, the interior surface including a first protecting group and the exterior surface including a second protecting group, the first and second protecting groups being selectively deprotected using a base and an acid.

Specific embodiments are directed to a method of forming the polymer bead(s). For example, a polymer bead having an interior surface and an exterior surface is caused to contact a first solution, which results in a first protecting group in the interior and exterior surfaces. The first solution can include the first protecting group. In specific embodiments, the contact can include reacting the polymer bead with a thiol-labile amine protecting group, such as DNs or Ns as described above. The method further includes causing the polymer bead to contact a second solution, which results in a topologically segregated polymer bead where the external surface includes a first deprotected group and the interior surface includes the first protecting group. In specific embodiments, the contact can include reacting the polymer bead with a first deprotecting group, which can include a protein having cysteines that selectively deprotect surface amines without deprotecting interior amines, such as BSA with TCEP.

The method can further include forming a library of screening compounds. A screening compound and encoding compound can be coupled to the polymer bead by constructing oligomers or polymers using surface-functionalized groups (e.g., the deprotected functional groups, such as free amine group). For example, the first deprotected group in the exterior surface is coupled to the screening compound and a second deprotected group in the interior surface is coupled to the encoding compound using a variety of chemical reactions. As described above, different protecting groups are coupled to the functional groups (e.g., amine groups) in the interior and exterior surface, which are used to control the reactions of the functional groups to build the screening and encoding compounds. As a specific example, the topologically segregated polymer bead is caused to contact a third solution that includes a second protecting group and resulting in the external surface including the second protecting group and the interior surface including the first protecting group. The first protected group in the interior surface is deprotected by causing the polymer bead to contact a fourth solution, which includes a second deprotecting group. The second deprotecting group can penetrate to the interior surface and resulting in a second deprotected group in the interior. The polymer bead is then caused to contact a fifth solution including a third protecting group and resulting in the external surface including the second protecting group and the interior surface including the third protecting group. The second and third protecting groups selectively deprotect using an acid and a base, and thereby allow for control of the location of the chemical coupling reactions used to build the screening compound and the encoding compound via acid and base deprotection.

Various embodiments further include performing acid and/or base deprotection. For example, the second protecting group is removed via base or acid decoupling resulting in the first deprotected group in the exterior surface. The first deprotected group is then coupled to a screening compound. Alternatively and/or in addition, the third protecting group is removed via base or acid decoupling resulting in a second deprotected group in the interior surface. The second deprotected group in the interior surface is then coupled to an encoding compound that can be used to label the screening compound. The steps can be repeated to form a library of polymer beads coupled to different screening compounds and encoding compounds. The library can be greater than 10^8 compounds large and can be used to screen for a reaction to at least one target, to generate a diagnostic assay, or for other target purposes/functions.

Embodiments in accordance with the present disclosure include all combinations of the recited particular embodiments. Further embodiments and the full scope of applicability of the invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various example embodiments may be more completely understood in consideration of the following detailed description in connection with the accompanying drawings, in which:

FIG. 5 illustrates an example process for topologically segregating a polymer bead, in accordance with various embodiments;

FIG. 6 illustrates an example process for topologically segregating a polymer bead, in accordance with various embodiments;

FIGS. 13A-13C illustrate example stability of a protecting group and deprotecting conditions, in accordance with various embodiments;

FIGS. 15A-15E illustrate example images of polymer beads, in accordance with various embodiments;

Figure 1A:
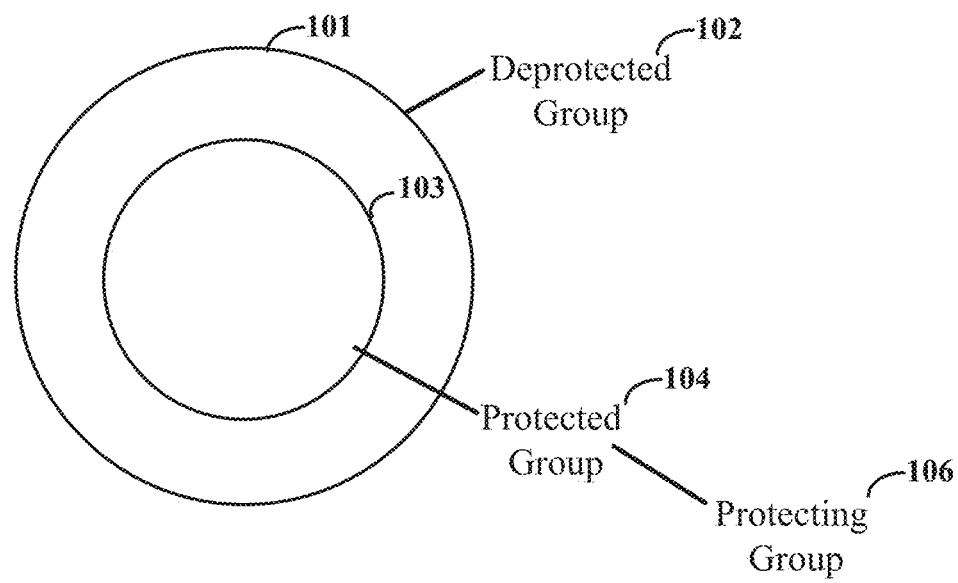
FIGS. 1A-1D illustrate examples of topologically segregated polymer beads, in accordance with various embodiments.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different polymer beads, methods of forming the same and methods for generating libraries of screening compounds. In certain implementations, a polymer bead has an interior surface and an exterior surface that are topologically segregated from one another. The interior surface has a protecting group and the exterior surface has a deprotected group. The topologically segregated bead can have surface-functionalized groups used to build a screening compound in the exterior surface and an encoding compound in the interior surface. While the present invention is not necessarily limited to such applications, various aspects of the invention may be appreciated through a discussion of various examples using this context.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element.

Various embodiments in accordance with the present disclosure are directed to a technique for forming a library of screening compounds. The library includes a plurality of polymer beads, each bead having a different screening compound attached thereto. The library can be used to screen for reaction of the screening compound to a target, generate a diagnostic assay, and/or identification of new compounds that provide specific functionality. Respective screening compounds that are hits (e.g., react to the target), are identified via encoding compounds such that the screening compounds can be used for diagnosis, treatment, or other purposes. The different encoding compounds have different femtomolar mass spectrometry sequencing sensitives, amino acid sequences, and/or otherwise act as barcodes that are readout through an analytical technique. For example, the encoding compound in the library each have different masses or sequences (e.g., amino acid sequences or nucleic acid sequences, such as deoxyribonucleic acid (DNA)) that can be identified using mass spectrometry or polymerase chain reaction (PCR). The respective masses can map to, e.g., via a map, key, or other association, a respective screening compound. The reacted bead can be used to identify the respective screening compound by separating the various compounds from the bead, performing mass spectrometry or PCR, and identifying a mass, amino acid sequence or nucleic acid sequence that is indicative of an encoding compound and (which maps to) a respective screening compound. The screening compound can be used to form a pharmaceutical product used to treat an organism, used for diagnosis purposes, a sensor, an enzyme, used as a material for a particular purpose or to provide a particular functionality, among other uses. Libraries formed in accordance with the present disclosure can be on an order of $10^8$ to $10^9$ or more compounds and can include beads that are sub-90 microns in diameter, such as 10 microns in diameter. The library can be screened using an optical scanner, as further described herein.

To form the above-described libraries, various embodiments include the formation of topologically segregated polymer beads which can be used to selectively build the screening compound in the exterior surface of the bead and the encoding compound in the interior surface of the bead. Surprisingly, embodiments in accordance with the present disclosure include formation of the topologically segregated polymer beads using thiol-labile amine protecting groups that can be selectively removed on the surfaces of the polymer beads. The removal is performed using free cysteines on a protein which is larger than the pores of the polymer beads. Due to the size of the protein, the protein may be unable to penetrate into the pores of the resin, but can still react with exterior surface protecting groups to selectively expose free amine groups in the exterior surface. This process can sometimes be referred to as "bead shaving."

In specific embodiments, the polymer bead is porous and can have an interior surface and an exterior surface that are topologically segregated with respect to one another. For example, the polymer beads are hollow, where a hollow cavity is defined by the interior surface. The free cysteines of the protein can selectively deprotect amine groups in the exterior surface without deprotecting amine groups in the interior surface of the bead. The protein can be Bovine Serum Albumin (BSA) which has a molecular weight of 66.5 kilodaltons (kDa) and may not penetrate into (the pores of) the polymer bead. Further, the disulfide bonds of BSA can be reduced to thiol with the use of tris(2-carboxyethyl) phosphine (TCEP). Nitrobenzenesulfonamides can be used as a protecting group in liquid or solid phase synthesis. Nitrobenzenesulfonamides can be deprotected using thiols. Specifically, a polymer bead is reacted with a nitrobenzenesulfonamide protecting group such that the protecting group is present on the interior and exterior surface of the polymer bead. The polymer bead is then reacted with the protein (e.g., BSA reacted with TCEP) resulting in the interior surface including the protecting group and the exterior surface including a deprotected group.

A number of embodiments are directed to a polymer bead that has an interior surface and an exterior surface that are topologically segregated from one another. The interior surface includes a protecting group and the exterior surface includes a deprotected group. As previously described, the protecting group can include a nitrobenzenesulfonamide group, such as DNs or Ns, which is used to protect an amine group in the interior surface of the bead. The deprotected group can include an amine group, such as $NH_2$.

Specific embodiments are directed to a method of forming the polymer bead(s). For example, a polymer bead having an interior surface and an exterior surface is caused to contact a first solution, which results in a protecting group in the interior and exterior surfaces. The first solution can include the protecting group, such as a thiol-labile amine protecting group. The method further includes causing the polymer bead to contact a second solution which forms a topologically segregated polymer bead where the exterior surface includes a deprotected group and the interior surface includes the protecting group.

Other specific embodiments include a polymer bead that has a topologically segregated interior surface from the exterior surface which include surface-functionalized groups used to build the screening compound and encoding compound. For example, the exterior surface can include a first functional group coupled to a first protecting group (e.g., Fmoc) and the interior surface can include a second functional group coupled to a second protecting group (e.g., Boc). The protecting groups can be used to provide control over the reaction of the first and second functional groups to build the screening and encoding compounds. For example, a first amine group in the exterior surface can be coupled to Fmoc and a second amine group in the interior surface can be coupled to Boc. The Fmoc group is removed using a base, such as piperidine, to expose the first amine group which can be used to build the respective screening compound. The Boc group is then removed using an acid, such as trifluoroacetic acid (TFA), to expose the second amine group, which can be used to build the encoding compound used to tag and/or sequence the screening compound. Although embodiments are not so limited and can include removing the Boc group first to build the encoding compound and then removing the Fmoc group to build the screening compound. Thereby, in some embodiments, the polymer bead has an interior surface and an exterior surface that are topologically segregated from one another, the exterior surface including a first deprotected group coupled to a screening compound and the interior surface including a second deprotected group coupled to an encoding compound.

In accordance with a number of specific embodiments, the above-described methods and/or polymer beads can be used to generate a library of 10^8 to 10^9 (or more) screening compounds. Each screening compound is attached to a single polymer bead, which includes a specific encoding compound. The library can be screened for hits to a target, such as using an optical scanner. An example of an optical scanner is a fiber optic scanner, which includes a fiber optic bundle array, a laser, and imaging circuitry (e.g., camera), such as Fiber-optic Array Scanning Technology (FAST). The FAST technology is based on the concept of "Xeroxing" a plate containing beads with a scanning laser and collecting a high resolution capture image of the plate using a densely packed fiber optic array bundle. The FAST system can allow for rapid scanning at speeds of between 1 million and 25 million cells per minute. For more specific and general information regarding an example FAST system, reference is made to Hsieh H B, Marrinucci D, Bethel K, et al., "High speed detection of circulating tumor cells", Biosensors and Bioelectronics, 2006; 21: 1893-1899, and Krivacic R T, Ladanyi A, Curry D N, et al., "A rare-cell detector for cancer", Proc Natl Acad Sci USA, 2004; 101: 10501-10504, each of which are fully incorporated herein by reference.

The screening can include using a library of a plurality of different beads having different screening compounds in the bead exterior and different encoding compounds on the bead interior. An assay is performed with the beads to identify screening compounds on the exterior exhibiting a particular function. The beads, which can be porous, can have pore sizes such that molecules or cells of a larger than the pore sizes cannot enter the beads (e.g., the interior surface). As a result, the molecules or cells may only interact with screening compound in the exterior surface. In specific examples, the assay can be used to bind to a protein, inhibit an enzyme, and/or neutralize or kill a cell, among other functions. The detected activity is assessed via a fluorescent readout of the assay using an optical scanner. Identified beads that are suspected of exhibiting the particular function or activity are identified based on the scan and removed from the screening plate and placed in wells or tubes. Removed beads are further processed to release the encoding compound on the bead interiors via chemical cleavage. In specific embodiments, the chemical cleavage is performed using a base, such as sodium hydroxide, that can cleave a linker molecule (e.g., polyacrylamide (PAM) linkers). The encoding compounds are then read out using an analytical technique, such as mass spectrometry or PCR.

As may be appreciated and as used herein, a polymer bead includes or refers to a polymer material formed in a three-dimensional shape, such as a sphere, an ellipsoid, oblate spheroid, and prolate spheroid shapes. Topologically segregated includes or refers to a polymer bead with an interior surface and exterior surface having different molecules and/or compounds therein. Exterior surface of the polymer bead includes or refers to the outside of the polymer bead, which may come in contact with the surrounding environment and/or solution. Interior surface of the polymer bead includes or refers to the inside of the polymer bead. The interior surface can define the hallow cavity of a hallow bead, for example. Protecting group includes or refers to a compound and/or molecule that is introduced into another compound and/or molecule by chemical modification of a functional group (e.g., $NH_2$) to obtain chemoselectivity in a subsequent chemical reaction. Protected group includes or refers to a molecule or compound that is protected by the protecting group, which can include a functional group or form thereof and is sometimes herein interchangeably referred to as a "protected functional group". Deprotecting group includes or refers to a compound and/or molecule which is used to remove a protecting group. For example, a deprotecting group can be used to chemically modify a compound and/or molecule to remove the protecting group and/or to obtain the functional group (e.g., the deprotected group). A deprotected group is sometimes herein interchangeably referred to as a "deprotected functional group". A deprotected group or a deprotected functional group includes or refers to a resulting molecule or compound formed by reacting another molecule or compound having a protected group with a deprotecting group, which results in exposing the functional group. The protected group and deprotected group (e.g., functional groups that are protected or not protected) can each include different forms of an amine group, such as NH and $NH_2$. Screening compound includes or refers to an oligomer or polymer formed in a library that is used to test for different functionalities, such as binding to a target, neutralizing or killing a target, and/or providing physical properties, among other functionalities. Encoding compound includes or refers to a peptide, oligomer, polymer, or other sequence of compounds or molecules which labels a respective screening compound. A library includes or refers to a plurality of different polymer beads coupled to screening compounds. A functional group includes or refers to a group of atoms and/or bonds within a molecule (e.g., the polymer bead) that are responsible for a characteristic chemical reaction of the molecule.

Turning now to the figures, FIG. 1A-1D illustrates examples of topologically segregated polymer beads, in accordance with various embodiments. The polymer beads can be formed from (e.g., starting from) M-NH$_2$ Tentagel beads that are around 10 microns in diameter. However, embodiments are not so limited and the beads can include a variety of diameters, such as sub-90 micron diameters. For example, the polymer beads can have a diameter in a range of 90 to 10 microns.

As illustrated by FIG. 1A, the polymer bead 100 has an interior surface 103 and an exterior surface 101 that are topologically segregated from one another. The interior surface 103 includes a protecting group 106 and the exterior surface 101 includes a deprotected group 102. Further, the protecting group 106 can be protecting a protected group 104 in the interior surface 103. The polymer beads can be porous, and can have a hollow cavity. The interior surface 103 can define the hollow cavity, as illustrated.

Figure 1B:
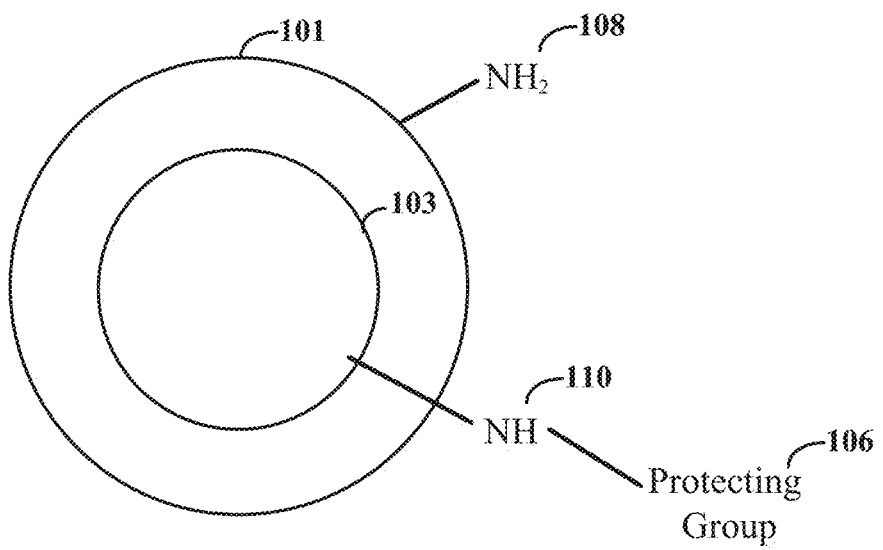

The deprotected group 102 can include an amine group. For example, as illustrated by FIG. 1B, a polymer bead 105 can have a deprotected group that is a primary amine (NH$_2$) 108 in the exterior surface 101 and the protected group can include an amine group (e.g., NH 110) coupled to the protecting group 106 in the interior surface 103.

Figure 1C:
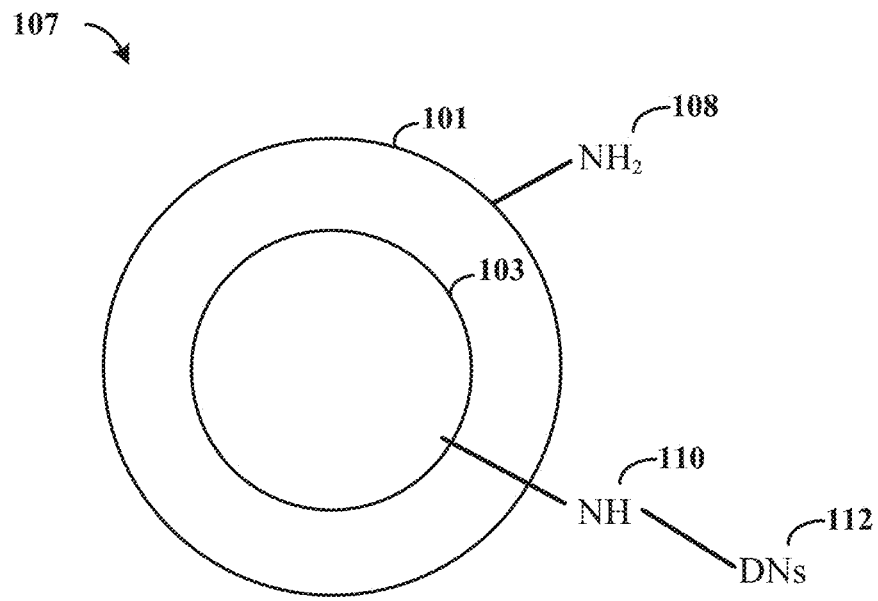
Figure 1D:
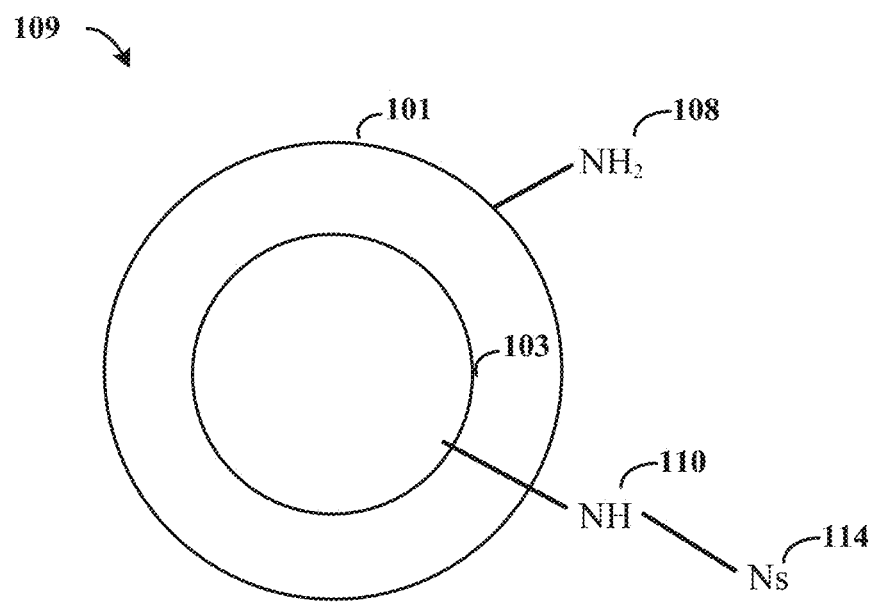

FIGS. 1C and 1D illustrate different examples of protecting groups, in accordance with various embodiments. The protecting group can include a nitrobenzenesulfonamide group, such as 2-4-Dinitrobenzenesulfonamides (DNs) and/or 2-nitrobenzenesulfonamide (Ns). For example, FIG. 1C illustrates a polymer bead 107 that includes NH$_2$ 108 in the exterior surface 101 and an amine group (e.g., NH 110) protected by a protecting group of DNs 112 in the interior surface 103. FIG. 1D illustrates a polymer bead 109 that includes NH$_2$ 108 in the exterior surface 101 and an amine group (e.g., NH 110) protected by a protecting group of Ns 114 in the interior surface 103.

The polymer beads illustrated by FIGS. 1A-1D can be used to generate a library of screening compounds. For example, the topological segregation of the interior surface 103 and the exterior surface 101 can be used to selectively couple a screening compound in the exterior surface 101 and an encoding compound in the interior surface 103. The library includes a plurality of polymer beads, each bead having a different screening compound attached thereto. The library can be used to screen for reaction of the screening compound to a target, generate a diagnostic assay, and/or identification of new compounds that provide specific functionality. Respective screening compounds that are hits are identified or otherwise sequenced. Each encoding compound in the library is associated with a respective screening compound and has different masses or sequences that can be identified using mass spectrometry or PCR. The respective masses or sequences can map to, e.g., via a map, key, or other association, to a respective screening compound. The reacted beads are used to identify the respective screening compound by separating the various compounds from the bead, performing mass spectrometry or PCR, and identifying a mass or a sequence that is indicative of an encoding compound which maps to a respective screening compound.

Figure 2:
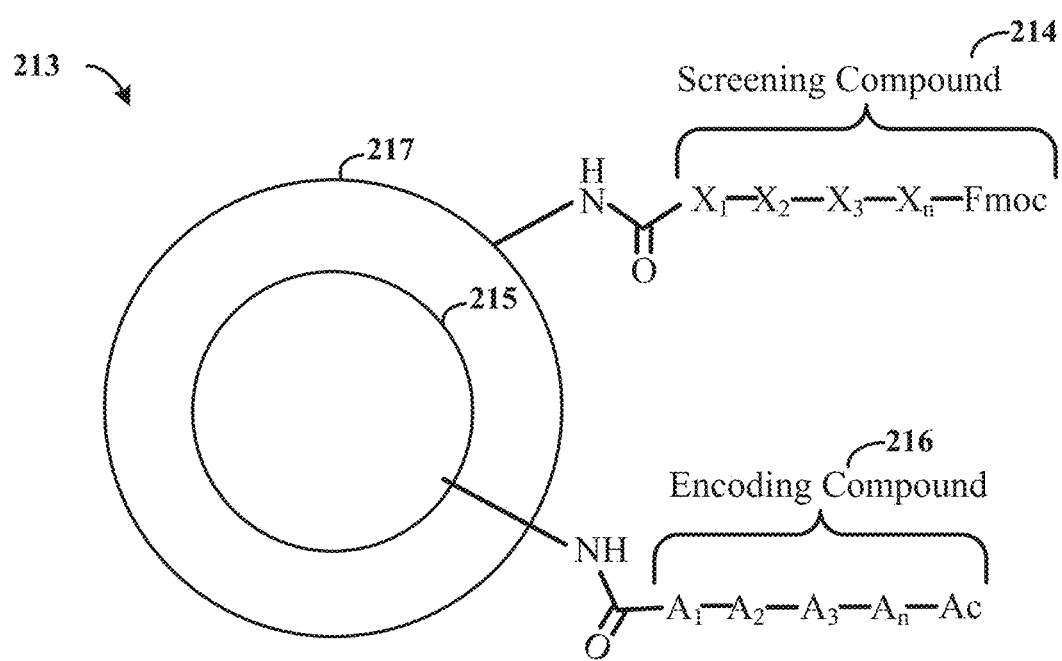
FIG. 2 illustrates an example of a topologically segregated polymer bead, in accordance with various embodiments.

FIG. 2 illustrates an example of a topologically segregated polymer bead, in accordance with various embodiments. The polymer bead 213 is topologically segregated via selective coupling of a screening compound 214 in the exterior surface 217 and an encoding compound 216 in the interior surface 215. In specific embodiments, the screening compound 214 is coupled to the deprotected group (e.g., a first functional group/NH) and the interior surface 215 includes another deprotected group (e.g., a second functional group/NH) coupled to the encoding compound 216. The encoding compound 216 is used to label the screening compound 214. For example, when a library of a plurality of polymer beads are screened, if the screening compound is a hit, the encoding compound 216 is used to identify the respective sequence of the screening compound 214, as described above.

Figure 3:
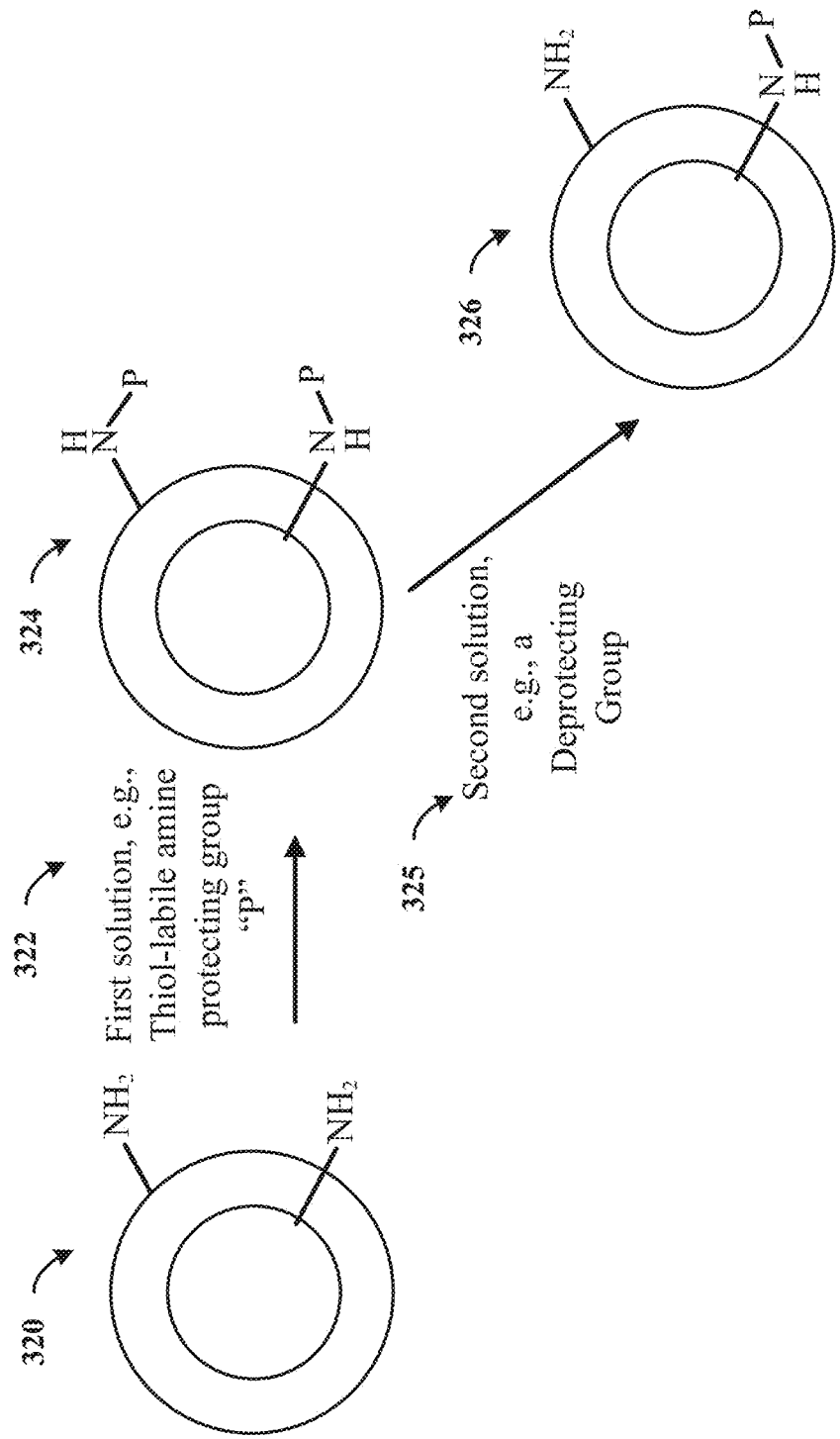
FIG. 3 illustrates an example process for topologically segregating a polymer bead, in accordance with various embodiments.

FIG. 3 illustrates an example process for topologically segregating a polymer bead, in accordance with various embodiments. As previously described, a starting polymer bead 320 can include M-NH$_2$ Tentagel beads. The polymer beads 320 are caused to contact a first solution at 322. The first solution can include a thiol-labile amine protecting group, which is labelled "P". The protecting group can include DNs or Ns, as previously described. In specific embodiments, the first solution includes the protecting group (e.g., DNs-chloride or DNs-CL, or Ns-chloride or Ns-Cl), N,N-diisopropylethylamine (DIPEA), and dichroolmethane (DCM). By contacting the bead 320 with the first solution, the resulting bead 324 is formed which includes a protecting group (e.g., P) in the interior and exterior surfaces. Contacting the polymer bead 320 with the first solution can include reacting the polymer bead with the protecting group, whereby the protecting group can deprotect in the presence of thiols.

The polymer bead 324 is then caused to contact a second solution at 325. The second solution can include a deprotecting group, such as a protein having cysteines that selectively deprotect surface amines without deprotecting interior amines. As previously described, the protein can be of a size that it cannot penetrate the pores of the polymer bead 324 to deprotect interior amines (e.g., BSA). The contact with the second solution at 325 results in the topologically segregated polymer bead 326, which is sometimes referred to as "bead shaving". The topologically segregated polymer bead 326 includes a deprotected group in the exterior surface (e.g., NH$_2$) and a protecting group in the interior surface.

Figure 4A:
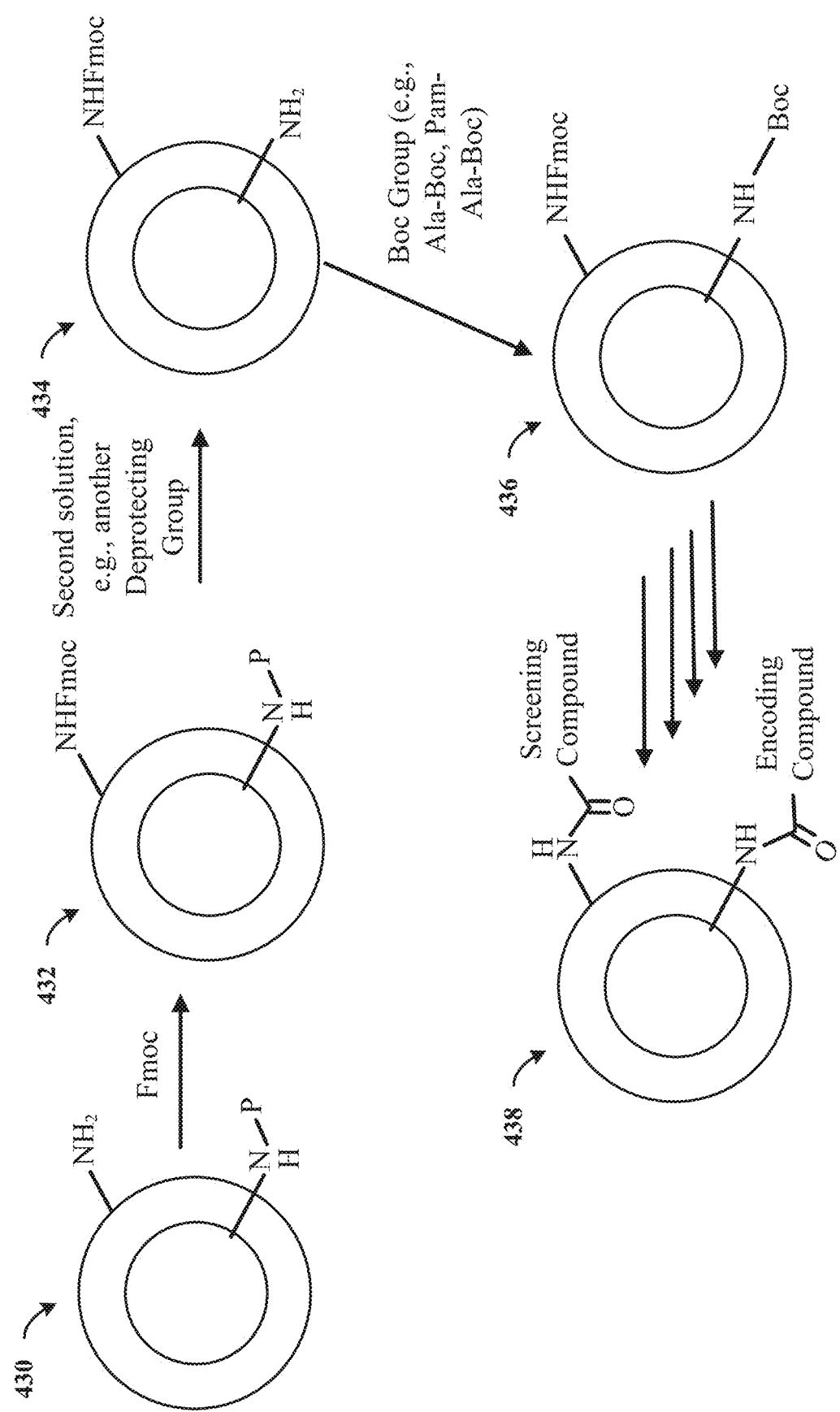
FIGS. 4A-4B illustrate an example process for topologically segregating a polymer bead, in accordance with various embodiments.
Figure 4B:
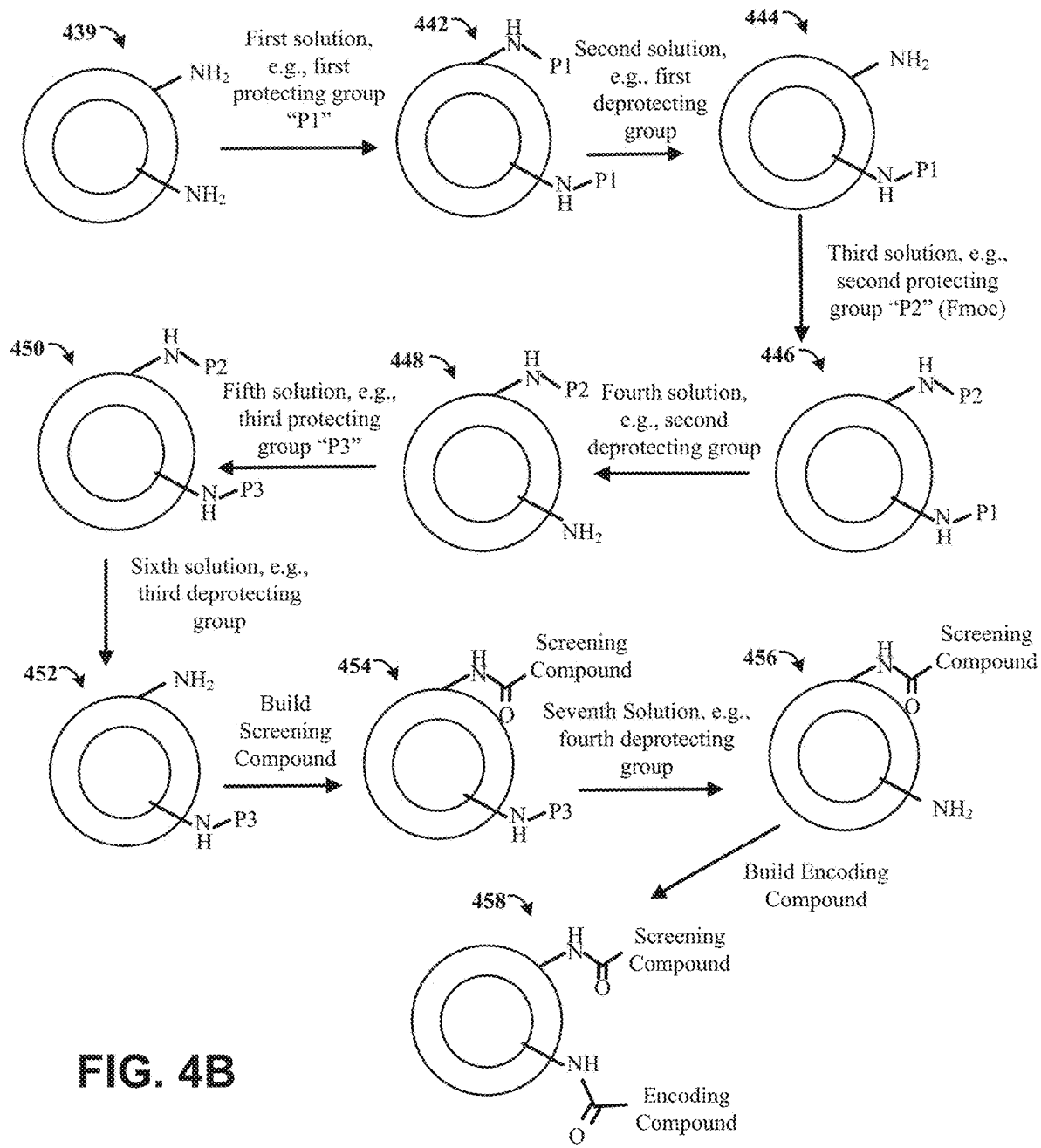

FIG. 4A illustrates an example process for topologically segregating a polymer bead, in accordance with various embodiments. A topologically segregated polymer bead 430 may be created using the process illustrated by FIG. 3, which can be further processed to generate a revised topologically segregated polymer bead 438 having a screening compound in the exterior surface and an encoding compound in the interior surface using surface-functionalized groups (e.g., free amines). The topologically segregated polymer bead 430 can be placed in contact with a first solution. The first solution can include another protecting group, such as an amine protecting group. For ease of reference, in the embodiment of FIG. 4A, the other protecting group is referred to as a "first protecting group", although in various embodiments the respective group is not the "first" protecting group in a sequence of reactions, as is illustrated by FIG. 4B. An example of an additional protecting group can include Fmoc. Placing the topologically segregated polymer bead 430 in contact with the first solution can cause a chemical reaction resulting in the polymer bead 432 having an amine group double coupled to the first protecting group (e.g., Fmoc) in the exterior surface of the bead 432.

The polymer bead 432 is then caused to contact a second solution (sometimes referred to a third solution) that includes another deprotecting group. The other deprotecting group can be of a size that the group can penetrate the pores of the bead but does not deprotect the first protecting group (e.g., Fmoc) in the exterior surface. The second solution can include a thiophenol solution (e.g., thiophenol (PhSH)). Contacting the polymer bead 432 with the second solution can result in deprotecting the protecting group in the interior surface, as illustrated by polymer bead 434 which has a deprotected group (e.g., $NH_2$) in the interior surface, and a protected group coupled to the first protecting group in the exterior surface (e.g., NHFmoc). An additional deprotecting group, such as a Boc group, is reacted with the polymer bead 434 to couple the deprotected group (now a protected group) in the interior surface to Boc, as illustrated by the polymer bead 436 having the protected group (e.g., another amine group) coupled to Boc in the interior surface. Example Boc groups include Ala-Boc and PAM-Ala-Boc. For ease of reference, in the embodiment of FIG. 4A, the additional protecting group is referred to as a "second protecting group", although in various embodiments the respective group is not the "second" protecting group in a sequence of reactions, as is illustrated by FIG. 4B.

In various embodiments, the first protecting group (e.g., Fmoc) in the exterior surface and the second protecting group (e.g., Boc) in the interior surface are used to cause the functional groups (e.g., the first and second amine groups) to be inert to various conditions. For example, the first functional group in the exterior surface is used to build a screening compound. The second functional group (e.g., the amine group) in the interior surface is used to build an encoding compound. The screening and encoding compounds are built using the functional amine groups via conventional chemical reactions and techniques, such as conventional coupling chemistry including peptide chemistry and solid-phase supported chemistry. Example techniques include assorted combinations of heat, pressure, and catalysis to alter chemical bonds, linear techniques, and repetitive bonding, among other techniques. For example, the functional groups can be reacted to form the polymer bead 438 having a screening compound in the exterior surface and an encoding compound in the interior surface. The first and second protecting groups are used to control where the chemistry is performed by allowing for controlled and selective reactions of the functional groups. Fmoc groups can be removed using a base, such as piperidine, to expose the first amine group and Boc groups can be removed using an acid, such as TFA, to expose the second amine group. Depending on whether the encoded compound or the screening compound is to be built first, the location of the chemical coupling is controlled by either an acid or base deprotection that exposes the respective amine group and leaves the other amine group protected.

Such a process can be used to form a plurality of different beads. Each bead has a different screening compound and encoding compound attached thereto. In specific embodiments, the plurality of beads can form a library of screening compounds which can be used to screen and identify synthetic oligomers and polymers with new functions. An example screening process can include screening for compounds that selectively bind to a molecular target, such as a protein or nucleic acid. Another example includes screening for compounds that neutralize or kill a target, such as tumor cells, virus-infected cells and/or bacterial cells. The screening molecules in the library can be used for various functions including pharmaceutical drugs, regents, sensors, catalysts, enzymes, or material used for particular purposes. The library can be screened to identify compounds (e.g., synthetic compounds) for different types of functions, which can include therapeutic, diagnostic, and/or industrial purposes.

The screening can include using a library of a plurality of different beads having different screening compounds in the bead exterior and different encoding compounds on the bead interior. An assay is performed with the beads to identify screening compounds on the exterior exhibiting a particular function. In specific example, the assay can be used to bind to a protein, inhibit an enzyme, and neutralize or kill a cell, among other functions. The detected activity is assessed via a fluorescent readout of the assay using an optical scanner. Identified beads that are suspect of exhibiting the particular function or activity are identified based on the scan and removed from the screening plate and placed in wells or tubes. Removed beads are further processed to release the encoding compound on the bead interiors via chemical cleavage, as previously described. The encoding compounds are then read out using an analytical technique, such as mass spectrometry or PCR.

FIG. 4B an example process for topologically segregating a polymer bead, in accordance with various embodiments. The embodiment of FIG. 4B can illustrate a combination process as illustrated by FIG. 3 and FIG. 4A. A starting polymer bead 439 is caused to contact a first solution containing a first protecting group, which is labelled "P1". The first protecting group can include DNs or Ns, as previously described. By contacting the bead 439 with the first solution, the resulting bead 442 is formed which includes a first protecting group (e.g., P1) in the interior and exterior surfaces.

The polymer bead 442 is then caused to contact a second solution. The second solution can include a first deprotecting group, such as a protein having cysteines that selectively deprotect surface amines without deprotecting interior amines. As previously described, the protein is of a size that it cannot penetrate the pores of the polymer bead 442 to deprotect interior amines. The contact with the second solution results in the topologically segregated polymer bead 444. The topologically segregated polymer bead 444 includes a deprotected group in the exterior surface (e.g., $NH_2$) and a first protecting group (e.g., P1) in the interior surface.

The topologically segregated polymer bead 444 is then placed in contact with a third solution. The third solution includes a second protecting group, such as an amine protecting group, which is labelled as "P2". An example of a second protecting group can include Fmoc. Placing the topologically segregated polymer bead 444 in contact with the third solution can cause a chemical reaction resulting in the polymer bead 446 having an amine group double coupled to the second protecting group (e.g., Fmoc) in the exterior surface of the bead 446 and another amine group coupled to the first protecting group (e.g., DNs or Ns) in the interior surface.

The polymer bead 446 is then caused to contact a fourth solution that includes second deprotecting group. The second deprotecting group can be of a size that the group can penetrate the pores of the bead but does not deprotect the second protecting group (e.g., Fmoc) in the exterior surface. The fourth solution can include a thiophenol solution (e.g., PhSH). Contacting the polymer bead 446 with the fourth solution can result in deprotecting the second protecting group in the interior surface, as illustrated by polymer bead 448 which has a deprotected group (e.g., $NH_2$) in the interior surface, and a protected group coupled to the second protecting group in the exterior surface (e.g., NHP2 or NHFmoc). The polymer bead 448 is then placed in contact with a fifth solution that includes a third protecting group, which is labelled as "P3". The third protecting group, such as a Boc group, reacts with the polymer bead 448 to couple the deprotected group (now a protected group) in the interior surface to the third protecting group. As illustrated by the polymer bead 450, the resulting bead has the first protected group (e.g., an amine group) coupled to the second protecting group and a second protected group (e.g., another amine group) coupled to the third protecting group (e.g., Boc) in the interior surface. Example Boc groups include Ala-Boc and PAM-Ala-Boc.

As previously described, the second and third protecting groups (P2 and P3) are used to allow for controlled reaction of the respective amine groups. To control where coupling chemistry is performed, acid or base deprotection is performed. Specifically, one of the second and third protecting groups can deprotect with a base and the other with an acid. As an example, the second protecting group (P2) is Fmoc that is removed with a base, such as piperidine, and the third protecting group (P3) is Boc that is removed with an acid, such as TFA. Although embodiments are not so limited. As an example, the polymer bead 450 is placed in contact with a sixth solution with includes a third deprotecting group. The third deprotecting group in this example removes the second protecting group (P2) to form the polymer bead 452. The polymer bead 452 has a free amine exposed in the exterior surface and a protected amine group in the interior surface. A screening compound is built using conventional couple chemistry to form the polymer bead 454 having a screening compound in the exterior surface and the protected functional group is coupled to the third protecting group in the interior surface. The polymer bead 454 is caused to contact a seventh solution that has a fourth deprotecting group used to deprotect the third protecting group (P3) in the interior, resulting in polymer bead 456 having the screening compound in the exterior surface and a free amine group in the interior surface. An encoding compound is built using conventional couple chemistry to form the polymer bead 458 having the screening compound in the exterior surface and an encoding compound in the interior surface.

Although the embodiment of FIG. 4B illustrates the screening compound being built followed by the encoding compound, embodiments are not so limited. In various embodiments, the third protecting group is first removed and the encoding compound is built, followed by removal of the second protecting group and building of the screening compound. Further, various specific embodiments can include a polymer bead having an interior surface and an exterior surface topologically segregated from one another, where the interior surface includes an encoding compound and the exterior surface includes a protecting group (e.g., Fmoc). As may be appreciated, embodiments in accordance with the present disclosure are not limited to performance of each of the steps illustrated by FIG. 4B and can be directed to performance of different sub-steps illustrated. Further, various embodiments are directed to one or more of the different polymer beads illustrated by FIG. 4B (e.g., 442, 444, 446, 448, 450, 452, 454, 456, 458). For example, the process can terminate at different steps of the process illustrated by FIG. 4B, resulting in different respective polymer beads.

FIG. 5 illustrates an example process for topologically segregating a polymer bead, in accordance with various embodiments. The process illustrated by FIG. 5 can include a specific example of the process previously described by FIG. 3. At 537, a polymer bead 535 is reacted with a solution including DNs to form a polymer bead 539 that includes a protecting group. The solution can include DNs-Cl, DIPEA, and DCM. The polymer bead 539 has a protecting group of DNs in the interior and exterior surfaces. The polymer bead 539 is then shaved by reacting with a protein with free cysteines, at 541. For example, the polymer bead 539 is reacted with a solution of BSA, TCEP, and buffer to form the polymer bead 543 having $NH_2$ in the exterior surface and DNs in the interior surface. The DNs group can be deprotected using thiophenonol (e.g., acid dissociation constant (pKa) of 6.6.), with varying pH (e.g., 6 and 6.5), using different buffers (e.g., phosphate, 2-(N-morpholino)ethanesulfonic acid (MES), 4-(2-hydroxyethyl)-1-piperazineethanesulfonic acid (HEPES)), with different concentrations of TCEP, BSA, 2,2,2-trifluoroethanol (TFE), and temperatures. In specific embodiments, a solution of 10 milligram (mg)/milliliter (mL) of BSA with 1.5 millimolar (mM) TCEP, 20% (v/v) TFE in phosphate buffer at pH of 6.5 at 4 degrees Celsius (C) incubated overnight is used.

FIG. 6 illustrates an example process for topologically segregating a polymer bead, in accordance with various embodiments. The process illustrated by FIG. 6 can include a specific example of the process previously described by FIG. 3. In various applications, microwaved assisted peptide synthesis is used to speed up reaction time and increase peptide use. DNs can be unstable under basic conditions at high temperatures. For more general and specific information of the stability of DNs at various temperatures, reference is made to Burns et al, "Selective Reduction of Disulfides by Tris(2-carboxyethyl)phosphine", J. Org. Chem 56, 2648-2650 (1991), which is hereby incorporated by reference in its entirety. A protecting group of Ns can be used in various embodiments which can be more stable than a DNs group under different conditions. At 647, a polymer bead 645 is reacted with a solution including Ns to form a polymer bead 649 including a protecting group. The solution can include Ns-Cl, DIPEA, and DCM. The polymer bead 649 has a protecting group of Ns in the interior and exterior surfaces. The polymer bead 649 is then shaved by reacting with a protein with free cysteines, at 651. For example, the polymer bead 649 is reacted with solution of BSA, TCEP, and buffer to form the polymer bead 652 having a $NH_2$ in the exterior surface and Ns in the interior surface. Ns, either in solid phase or aqueous phase, can be removed using a thiophenolate anion (e.g. HSCH2CO2H/K2CO3, thiophenol/K2CO3), to mimic conditions, and different pH for the deprotection of the exterior surface of the beads can be used. In specific embodiments, a solution of 10 mg/mL of BSA with 1.5 mM TCEP, 20% (v/v) TFE in phosphate buffer pH 8.5, for 2 hours at 40 degrees C. is used. Further, decreasing the pH can increase the deprotection of the Ns-group inside the bead.

Figure 7A:
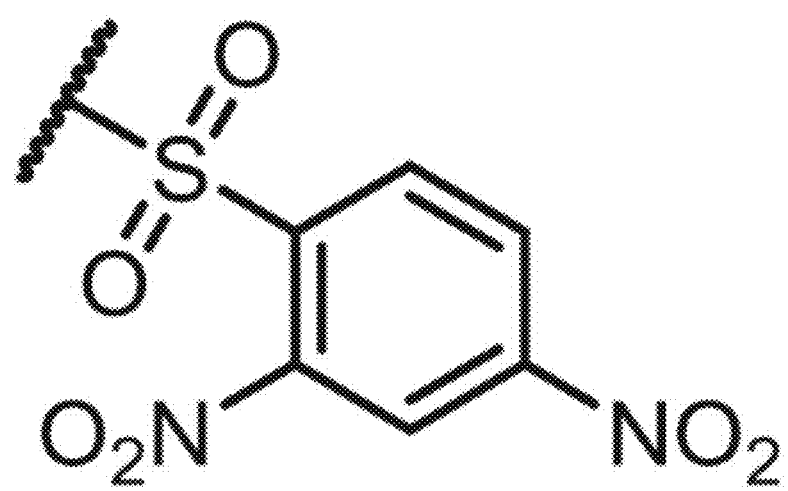
FIGS. 7A-7B illustrate examples of protecting groups, in accordance with various embodiments.
Figure 7B:
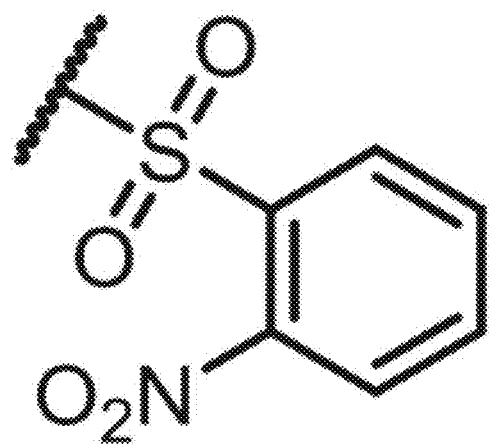

FIGS. 7A-7B illustrates examples of protecting groups, in accordance with various embodiments. Specifically, FIG. 7A illustrates an example of DNs and FIG. 7B illustrates an example of Ns. DNs can be deprotected at lower temperatures with thiol treatments, and are thereby more easily shaved. Ns can be deprotected at higher temperatures with greater stability than DNs.

Various embodiments include the surprising results of topologically segregated polymer beads. Specific embodiments include methods for spatial segregation of 10 micron Tentagel beads using reduced BSA for the deprotection of nitrobenzenesulfonamide groups present on the surface of the beads. The methods can be applied to the synthesis of polymer beads having Fmoc protecting group on the outside layer and Boc group on the inside.

MORE DETAILED/EXPERIMENTAL
EMBODIMENTS

As previously described, to screen libraries on the order of 10^8 to 10^9 or more compounds, polymer beads that are sub-90 microns are used. In various embodiments, the bead sizes include 10 micron diameter resin. In order to screen libraries formed using beads of such size, the resulting screening compounds can be analyzed using mass spectrometry (MS) techniques that ionizes the compounds and sorts ions based on their mass-to-charge ratio or using PCR techniques. The amount of material required to sequence the screening compounds can be a limitation. As described above, various embodiments include the use of encoding compounds used to identify the screening compound. For example, in experimental embodiments, sub-femtomolar amounts of material can be measured by MS and/or PCR by combining the screening compound with the encoding compound. To form the library, topologically segregated polymer beads are used to form interior functional groups as encoding elements and surface-functionalized (e.g., exterior) groups for screening compound (e.g., polymer) construction. The topologically segregated polymer beads can be formed using thiol-labile amine protecting groups that can be removed by cysteines on proteins.

Various experimental embodiments can be used to demonstrate the topological segregation of the polymer beads which are formed using the above described methods. The topologically segregated polymer beads can be experimentally obtained using M-NH$_2$ Tentagel beads (10 micron) and various compounds and/or solutions that can be commercially obtained. For example, TentaGel® M NH$_2$ (loading 0.25 mM/gram (g), 10 millimeter (mm)) can be commercially obtained from Rapp Polymere. Hydroxybenzotriazole (HOBt) (e.g., 1-hydroxybenzotriazole) and Fmoc-Ala-OH can be purchased from Chem-Impex International. DIPEA, Diisopropylcarbodiimide (DIC) (1,3-diisopropyl-carbodiimide), Fluorescein-5-isothiocyanate (FITC), tris(2-carboxyethyl)phosphine, all organic solvents, and other chemical reagents can be purchased from Aldrich. Bovine Serum albumin can be from Fisher Scientific. Boc-Ala-OCH2-Phenyl-CH2-COOH can be purchased from PolyPeptide. Confocal laser scanning microscope (CLSM) can be used to verify the structure.

Figure 8C:
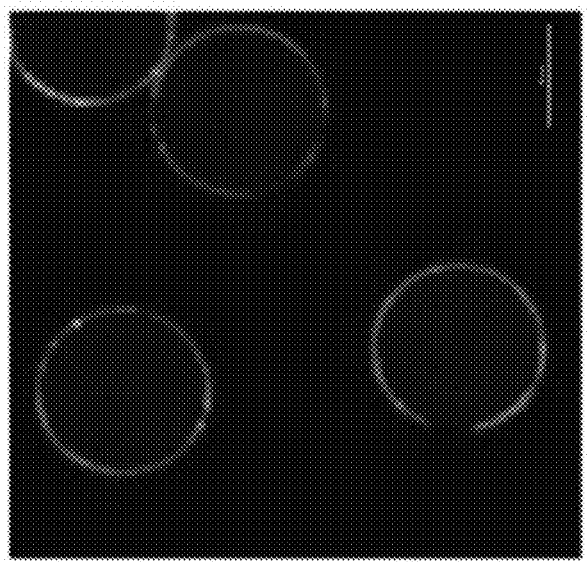
FIGS. 8A-8C illustrate example images of experimentally obtained polymer beads, in accordance with various embodiments.
Figure 8B:
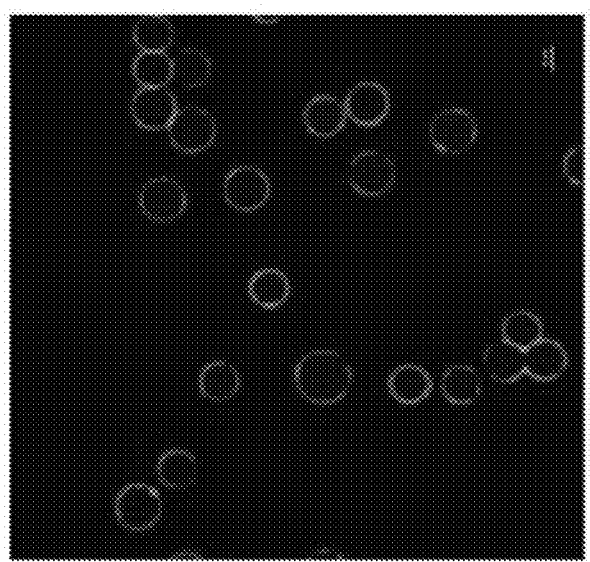
Figure 8A:
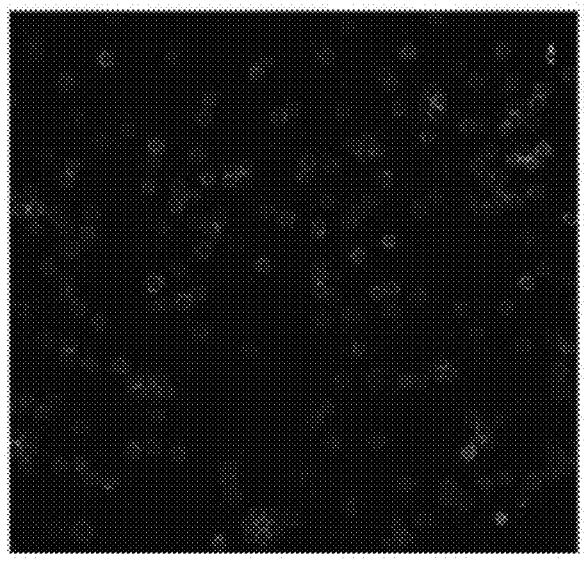

FIGS. 8A-8C illustrates example images of experimentally obtained polymer beads, in accordance with various embodiments. The images are of topologically segregated polymer beads that are segregated using a DNs protecting group, such as via the method illustrated above by FIG. 5. The images include CLSM images of the polymer beads. The distribution of amino groups on the resin is visualized via FITC labeling on a CLSM. The FITC dye is used to covalently label amine groups for visualization by CLSM. The CLSM images can be obtained at 20× (FIG. 8A), 60× (FIG. 8B) and 60× zoom 4 (FIG. 8C). As illustrated, the FITC (e.g., green) labeling is present on the exterior surface, thus confirming the deprotected group (the amine group) is present in the exterior surface and the protecting group is present in the interior surface. Reactions at room temperature can lead to a complete deprotection of the bead, along an increase in TFE concentration (up to 50% v/v). The later can be due to TFE acting as a conformation effector. Use of 6M guanidine-HCL or 8M urea as a denaturant may not improve the reaction. As illustrated in FIG. 8C, the FITC labeling may not be uniform as the beads can have hollow cavities.

Figure 9C:
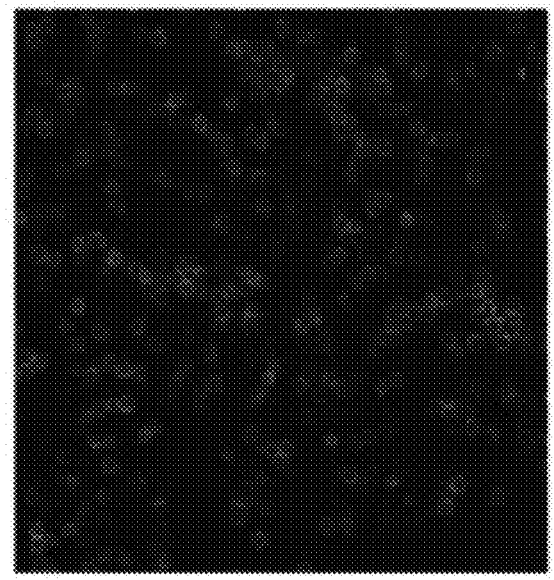
FIGS. 9A-9C illustrate example images of experimentally obtained polymer beads, in accordance with various embodiments.
Figure 9B:
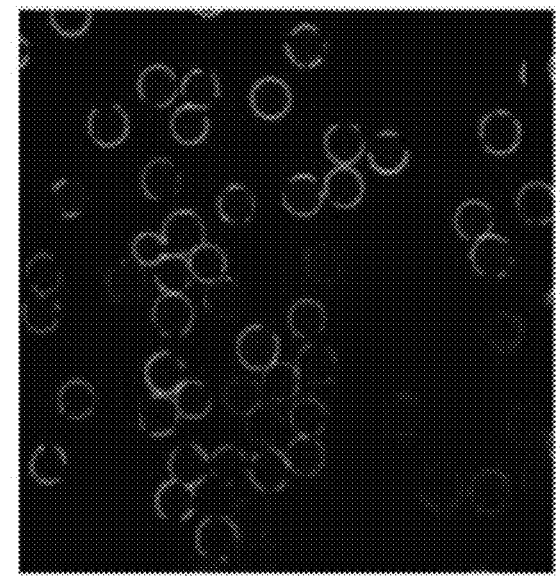
Figure 9A:
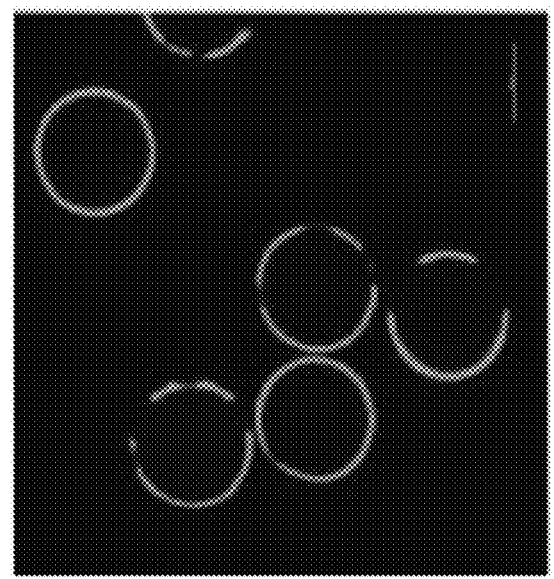

FIGS. 9A-9C illustrate example images of experimentally obtained polymer beads, in accordance with various embodiments. The images are of topologically segregated polymer beads that are segregated using an Ns protecting group, such as via the method illustrated above by FIG. 6. The images include CLSM images of the polymer beads. As previously described, decreasing the pH can increase the deprotection of the Ns-group inside the bead. FIG. 9A illustrates polymer beads obtained at pH 9, FIG. 9B illustrates polymer beads obtained at pH 8, and FIG. 9C illustrates polymer beads obtained at pH 7.

Figure 10:
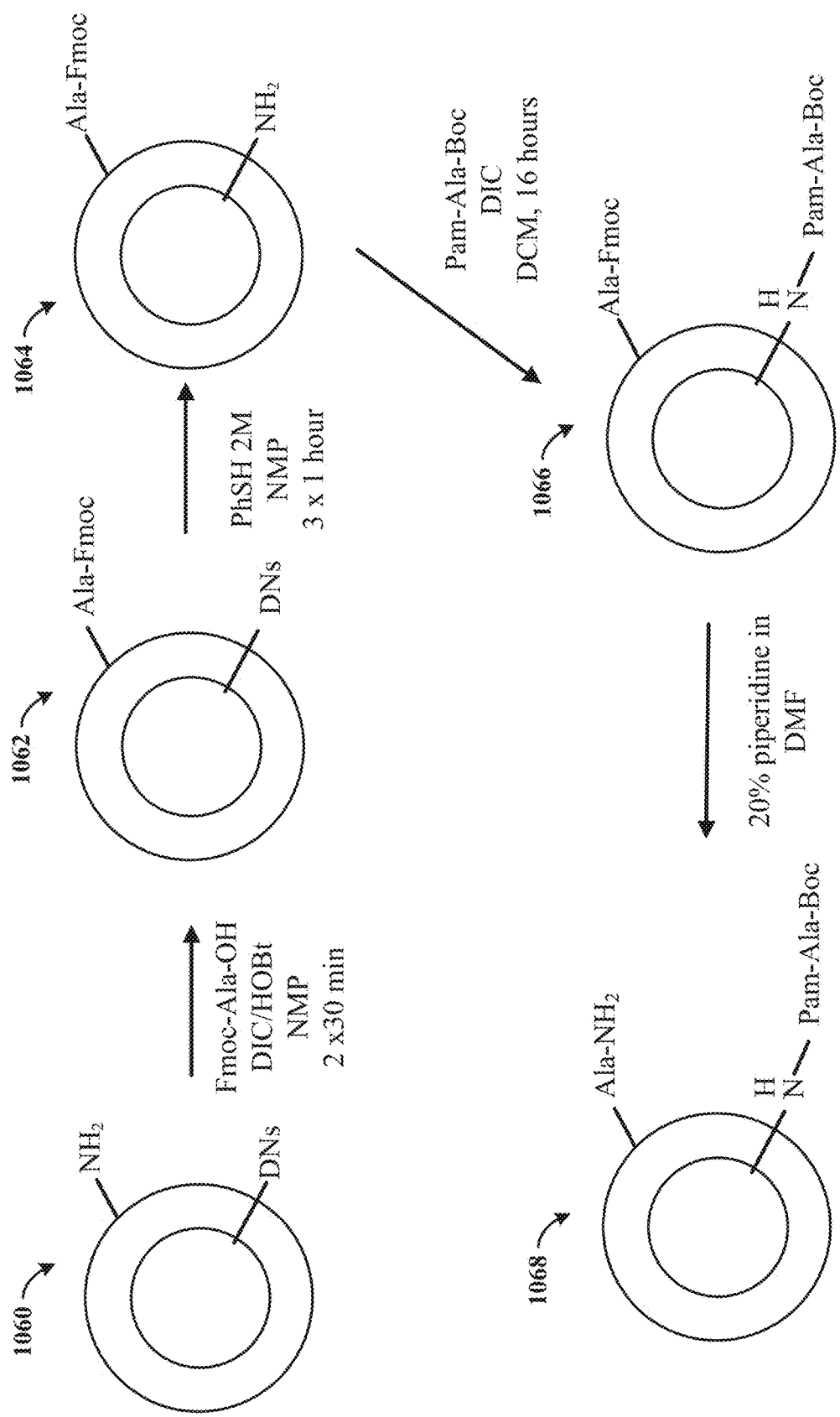
FIG. 10 illustrates example of a process for topologically segregating a polymer bead, in accordance with various embodiments.

FIG. 10 illustrates an example process for topologically segregating a polymer bead, in accordance with various embodiments. As previously described, such as via the method illustrated by FIGS. 3 and 4A-4B, a topologically segregated polymer bead 1060 can be further reacted to form a revised topologically segregated polymer bead 1068 having a screening compound in the exterior surface and an encoding compound in the interior surface. The topologically segregated polymer bead 1060 having a DNs protecting group in the interior surfaces and NH$_2$ in the exterior surface is reacted with a solution that includes Fmoc. More specifically, the free amine group (NH$_2$) in the exterior surface is doubled coupled with Fmoc-Ala-OH using DIC/HOBt to give the polymer bead 1062. The DNs protecting group is removed using a 2M thiophenol solution to give a free amine group in the interior surface, resulting in polymer bead 1064. Boc-Ala-PAM-OH is coupled to the amine group in the interior surface using DIC to form the polymer bead 1066. The Fmoc and Boc groups can be used to selectively control building of the screening and encoding compounds, as previously described. To demonstrate that the polymer bead 1064 remains topologically segregated, Fmoc deprotection can be performed using piperidine to yield a free amine group in the exterior surface and by using an amine-reactive dye to demonstrate the revised topologically segregated polymer bead 1068 that is topologically segregated.

Figure 11B:
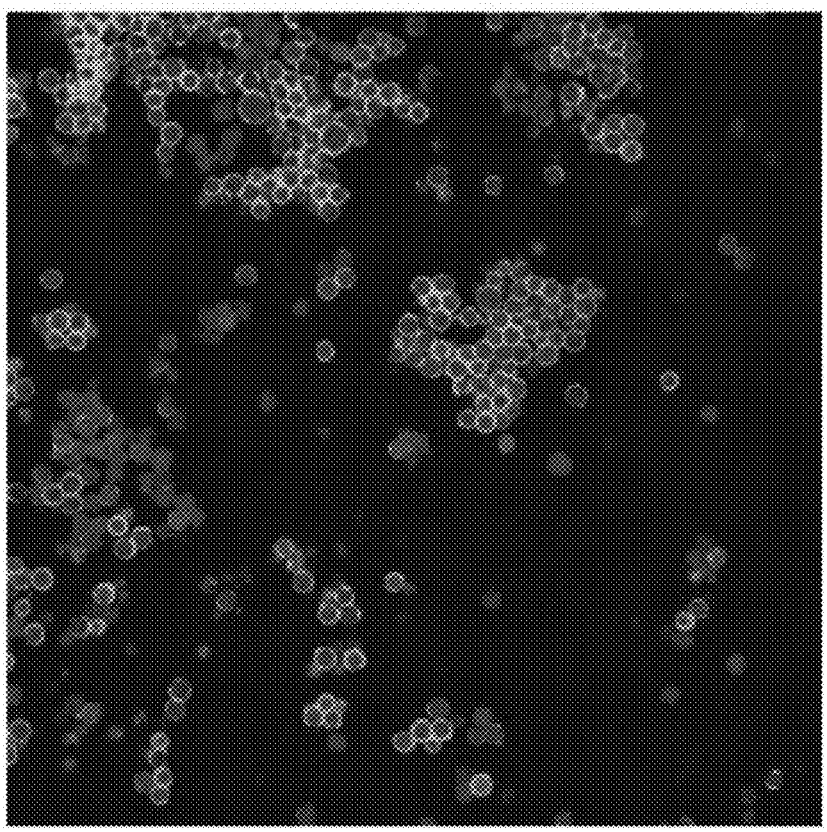
FIGS. 11A-11B illustrate example images of polymer beads experimentally obtained via the process of FIG. 10, in accordance with various embodiments.
Figure 11A:
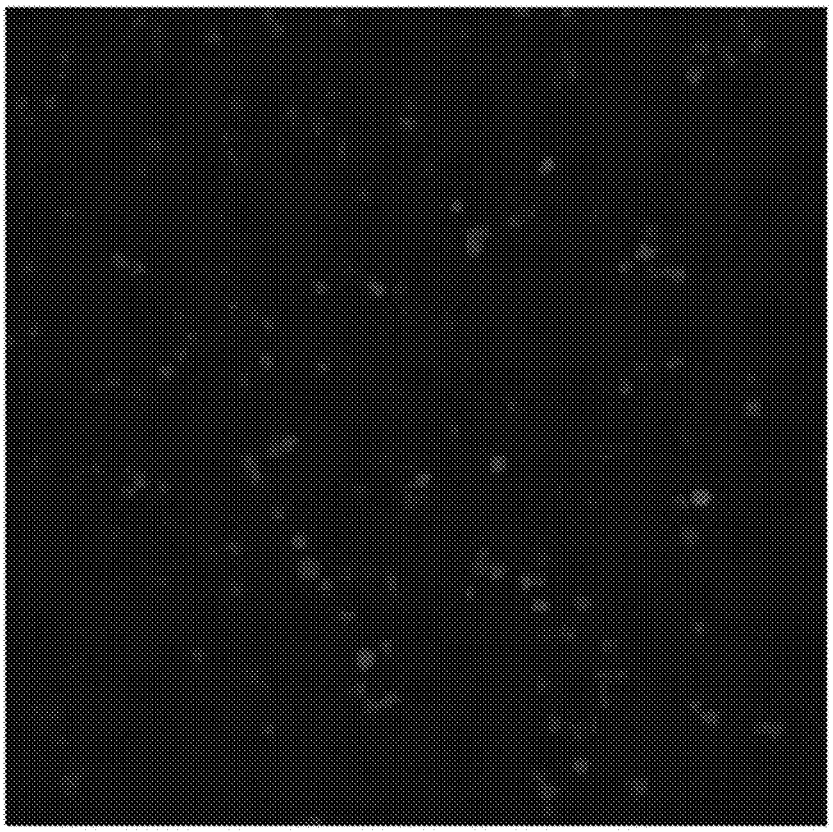

FIGS. 11A-11B illustrates example images of polymer beads experimentally obtained via the process of FIG. 10, in accordance with various embodiments. FIG. 11A illustrates an image of the polymer beads 1066 and FIG. 11B illustrate an image of the polymer beads 1068 as labeled with FITC to identify free amine groups. As the polymer beads 1066 do not include free amine groups, the blue color (e.g., which represents autofluorescence of the beads) show beads that lack any green FITC labeling which demonstrates that the amines are protected. The polymer beads 1068 include free amine groups in the exterior and not in the interior, which is illustrated by the green color in the exterior and blue color in interior of the beads and demonstrates that the polymer beads 1068 are layered or topologically segregated.

FITC labeling can be achieved in various experimental embodiments by placing 20 mg of resin in an Eppendorf tube in 150 microliter (μL) of DMF and sonicated 30 seconds. Then 97 μL of FITC in DMF (1 mg/mL) and 114 μL of DIPEA in DMF (1 mg/mL) is added. The resin solution is vortex for 30 seconds and placed on a rotator in the dark for 2 hours. After filtration and washing with DCM (3 times), DMF (3 times), and DCM (3 times). The labeled beads are placed on Superfrost® Plus microscope slide. A cover slip can be placed on top of the beads solution and glued.

A number of experimental embodiments include a procedure for dinosylation (e.g., DNs) on solid phase. For example, in a peptide vessel 1 g of resin is covered in DCM and allowed to swell for 1 hour. 2,4-dinitrobenzenesulfonyl chloride (10 eq, 666 mg) is dissolved in DCM (10 mL). The solution is added to the resin followed by DIPEA (9.1 eq, 348 ul), swirled, covered and stand at room overnight. After filtration, the resin is washed with DCM (3 times), dimethylformamide (DMF) (3 times), and DCM (3 times).

A number of experimental embodiments include a procedure for nosylation (e.g., Ns) on solid phase. In a peptide vessel 2 g gram of resin is covered in DCM and allowed to swell for 1 hour. 2-nitrobenzenesulfonyl chloride (10 eq, 973 mg) is dissolved in DCM (20 mL). The solution is added to the resin followed by DIPEA (9.1 eq, 697 ul), swirled, covered and stand at room overnight. After filtration, the resin is washed with DCM (3 times), DMF (3 times), and DCM (3 times).

Various experimental embodiments include dinosylated (e.g., DNs) bead segregation. For example, on a 45 mL falcon tube, 400 mg of BSA is dissolved in 32 mL of cold phosphate buffer and 9 mL of TFE. 1.5 mM of TCEP solution is added and the pH adjusted to 6.5. Then 500 mg of dinosylated beads are suspended in the BSA solution, sonicated and place in a rotator overnight at 40 degrees C. After filtration, the solution is washed with Guanidine 6M (3 times), DCM (3 times), DMF (3 times), and DCM (3 times).

Various experimental embodiments include nosylated (e.g., Ns) bead segregation. For example, in a 45 mL falcon tube, 400 mg of BSA is dissolved in 32 mL of cold phosphate buffer and 9 mL of TFE. 1.5 mM of TCEP solution is added and the pH adjusted to 9. Then 500 mg of dinosylated beads are suspended in the BSA solution, sonicated and placed in a shaker at 370 degrees C. overnight. After filtration, the solution is washed with Guanidine 6M (3 times), DCM (3 times), DMF (3 times), and DCM (3 times).

The above illustrated polymer bead 1068 can be synthesized by first attaching Fmoc-Ala-OH. Fmoc-Ala-OH is dissolved in 0.4 M HOBt in DMF, and DIC is added. The solution is mixed and after 10 seconds is added to the peptide-resin. It is allowed to react 30 minutes at room temperature and flow washed for around 10 seconds with DMF. The reaction can be monitored by chloranil test as the Kaiser test in the presence of DNs-group can give false positive results. The DNs-group can then be removed by adding a 2M thiophenol solution to the peptide-resin and letting the solution react three times for one hour at room temperature and flow washed for around 10 seconds with DMF. The Boc-Ala-OCH2-Phenyl-CH2-COOH can then be attached. Boc-Ala-OCH2-phenyl-CH2-COOH can be dissolved in minimum volume of DCM. DIC is added, shaken to mix well and left at room temperature for 1-2 minutes before adding to the resin. The vessel is capped and the coupling reaction is allowed to proceed at room temperature overnight and flow washed for around 10 seconds with DCM. The Fmoc group can then be removed by adding 20% (volume/volume (/v/v)) of 4-methylpiperidine in DMF and letting the solution react for 5 minutes and this procedure can be repeated once more for 10 minutes. After filtration, the solution is flow washed with DMF. After each coupling and deprotection the Kaiser test can be done.

Figure 12:
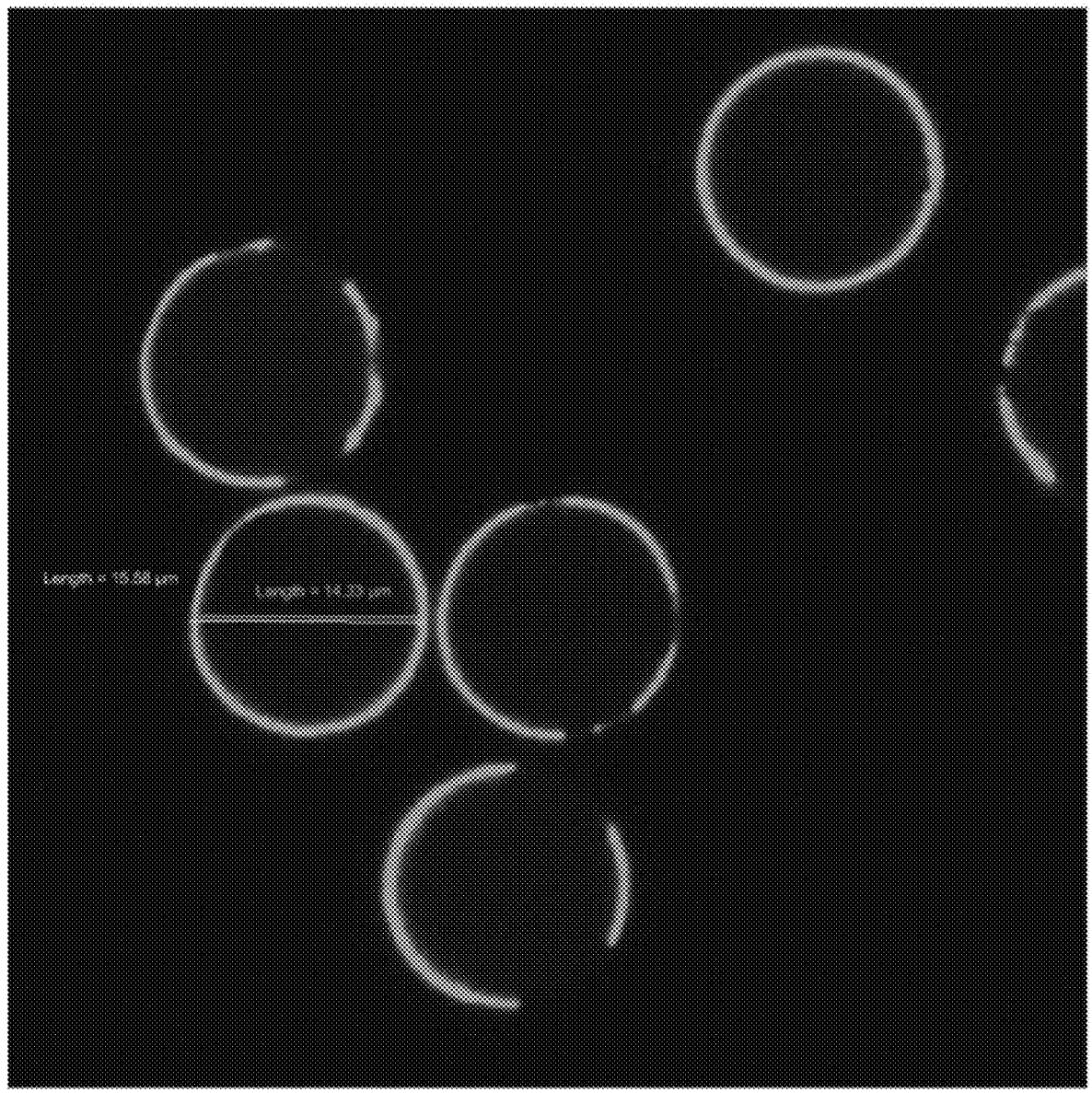
FIG. 12 illustrates an example image of experimentally obtained polymer beads, in accordance with various embodiments.

FIG. 12 illustrates an example image of experimentally obtained polymer beads, in accordance with various embodiments. The images can include CLSM images of FITC labeled shaved Ns-beads (e.g., beads that have the Ns protecting group shaven). The polymer beads can be shaved using 20% TFE in phosphate buffer pH 8.5, 1.5 mN TCEP, 4 degrees C. for two hours.

Figure 13C:
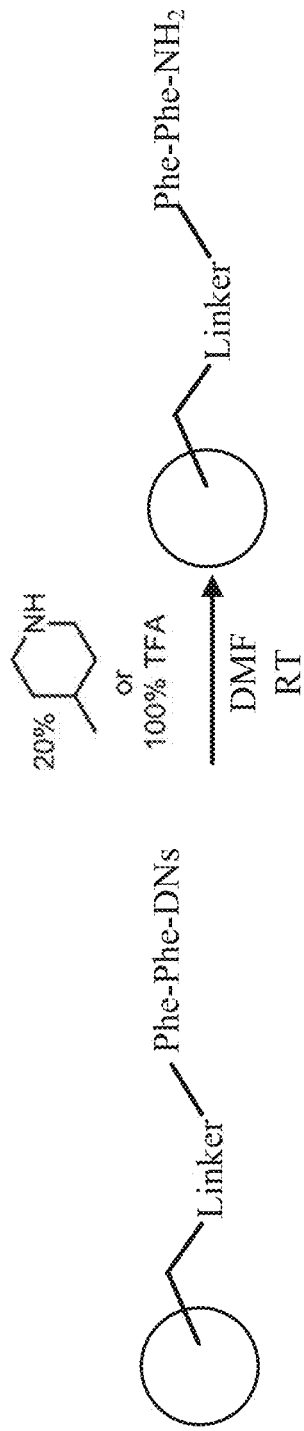

FIGS. 13A-13C illustrates example stability of a protecting group and deprotecting conditions, in accordance with various embodiments. The protecting group can be DNs in the embodiments illustrated by FIGS. 13A-13C. As illustrated by FIG. 13A, the DNs group can be deprotected with 10M PhSH in DMF, room temperature (RT), for one hour. In experimental embodiments, a range of 0.5-10M PhSH with one hour reaction times can be tested. FIG. 13B illustrates the mass spectrometry analysis of the cleaved product. The DNs group can be stable in acidic conditions but not stable in basic conditions. FIG. 13C illustrates treatment of a DNs group with 100% TFA and treatment with 20% 4-methylpiperiding. In experimental embodiments, two 5 minute treatments of the DNs group with 100% TFA results in around 3% DNs removal and two 5 minute treatments of the DNs group with 20% 4-methlypiperiding results in 97% DNs removal.

In a number of experimental embodiments, the optimized bead shaving conditions with DNs can be explored. Bead shaving DNs protecting groups with BSA as a macromolecular source of reactive thiol groups can be used to topologically segregate a polymer bead. Reaction variables that can be varied include type and concentration of denaturant (e.g., 8M urea, 6M guanidine, TFE), time and temperature of the reaction, concentration of the reducing reagent (e.g., TCEP), and buffer type and pH. In various specific embodiments, the optimal conditions can include 20% TFE in phosphate buffer pH 6.5, 1.5 mM TCEP, 4 degrees C., overnight, although embodiments are not so limited.

Figure 14A:
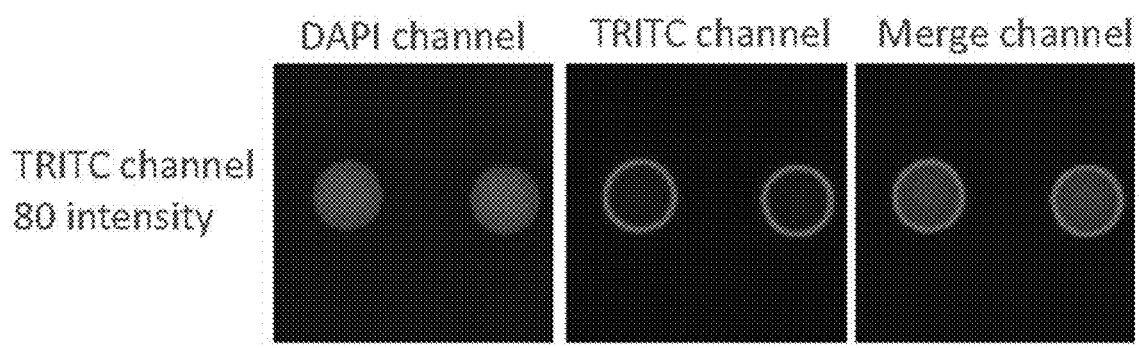
FIGS. 14A-14D illustrate example images of experimentally obtained polymer beads and non-segregated polymer beads, in accordance with various embodiments.
Figure 14B:
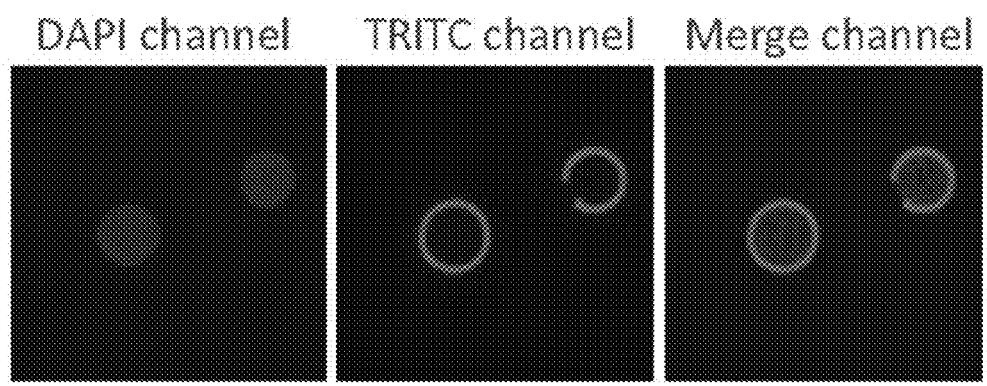
Figure 14C:
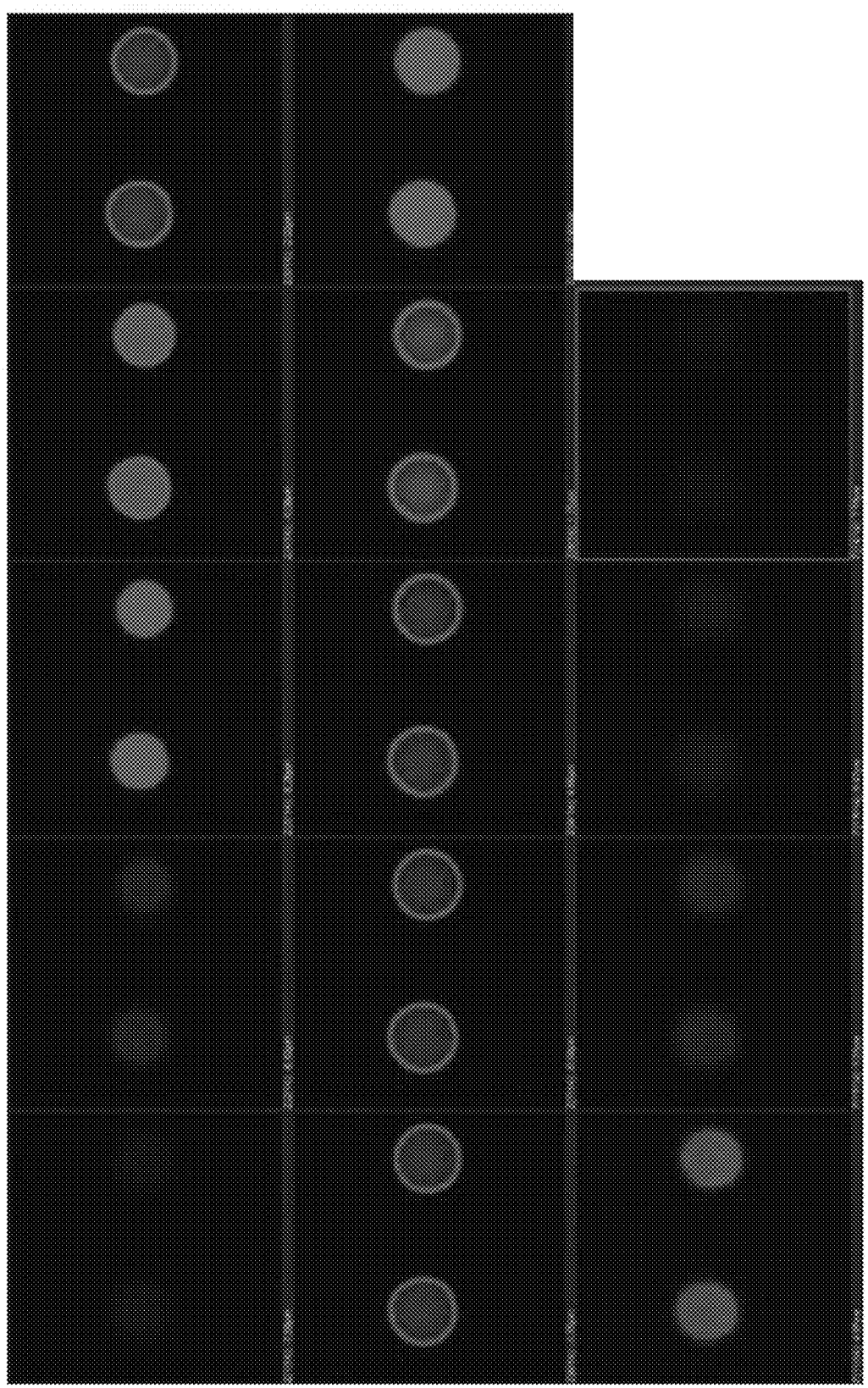
Figure 14D:
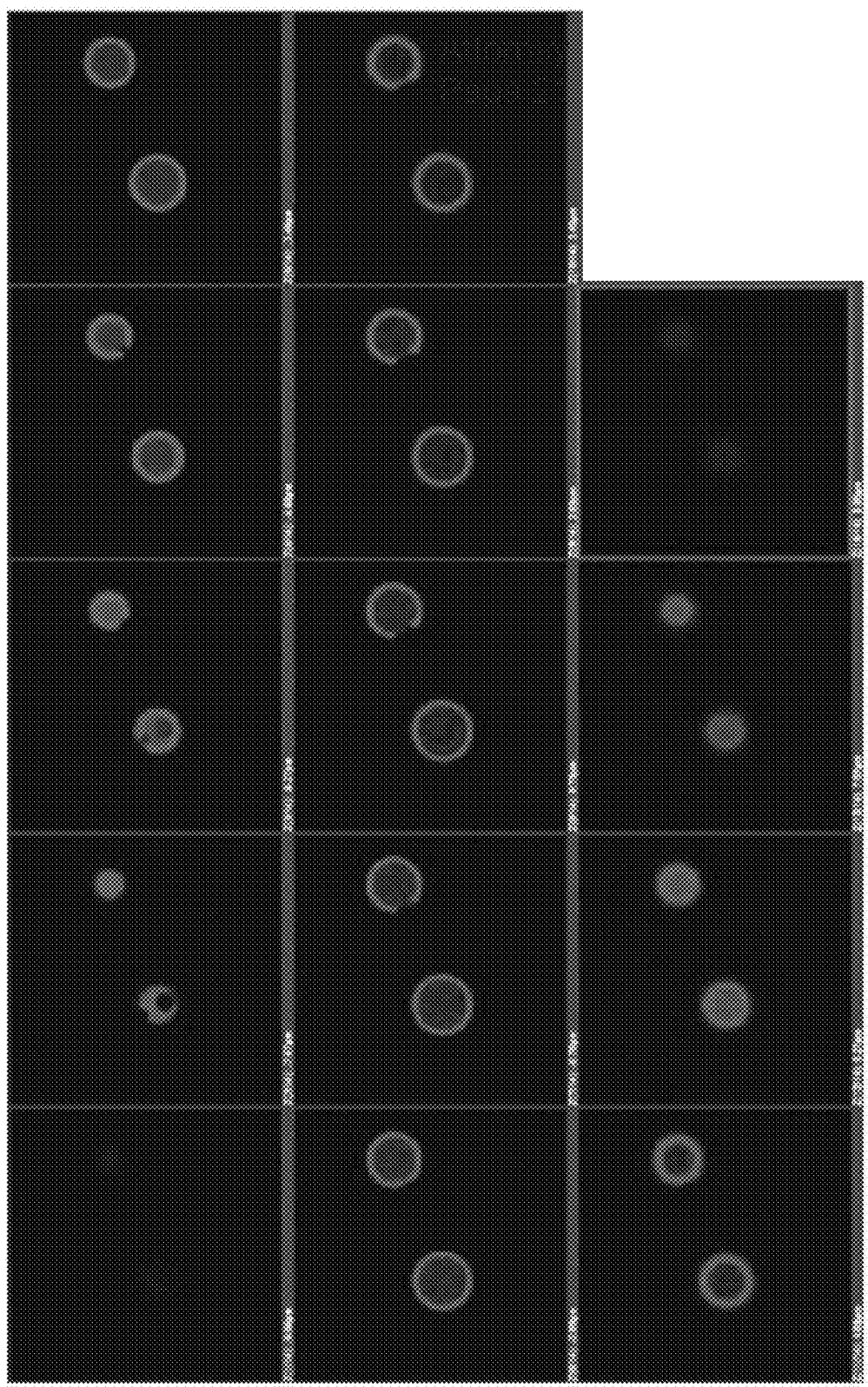

FIGS. 14A-14D illustrates example images of experimentally obtained polymer beads and non-segregated polymer beads, in accordance with various embodiments. The non-segregated polymer beads can include non-shaved beads. The particular beads are labeled with SA AF555 (e.g., Alexa Fluor® 555 streptavidin) which can include a biotin-binding protein (e.g., strepavidin) covalently attached to a fluorescent label. The beads are then imaged using an optical system, such as a microscope. For example, the images illustrated by FIGS. 14-14D can include confocal images at 60× and zoom 4. The optical system used to image the beads can have multiple channels, such as a 4',6-diamidino-2-phenylindole (DAPI) channel (e.g., blue) and a tetramethylrhodamine isothiocyanate (TRITC) channel (e.g., red). FIG. 14A illustrates images of the non-segregated polymer beads labelled with SA AF555 (e.g., 11A beads), as imaged using the DAPI channel, TRITC channel, and merged channel (e.g., both the DAPI and TRITC channels). FIG. 14B illustrates images of topologically segregated polymer beads labelled with SA AF555 (e.g., 23E beads) and as imaged using the DAPI channel, TRITC channel, and merged channel. FIGS. 14C and 14D illustrate Z-stack of bead cross sections from top to bottom of the non-segregated polymer beads (e.g., FIG. 14C) and the topologically segregated polymer beads (e.g., FIG. 14D).

Figure 15E:
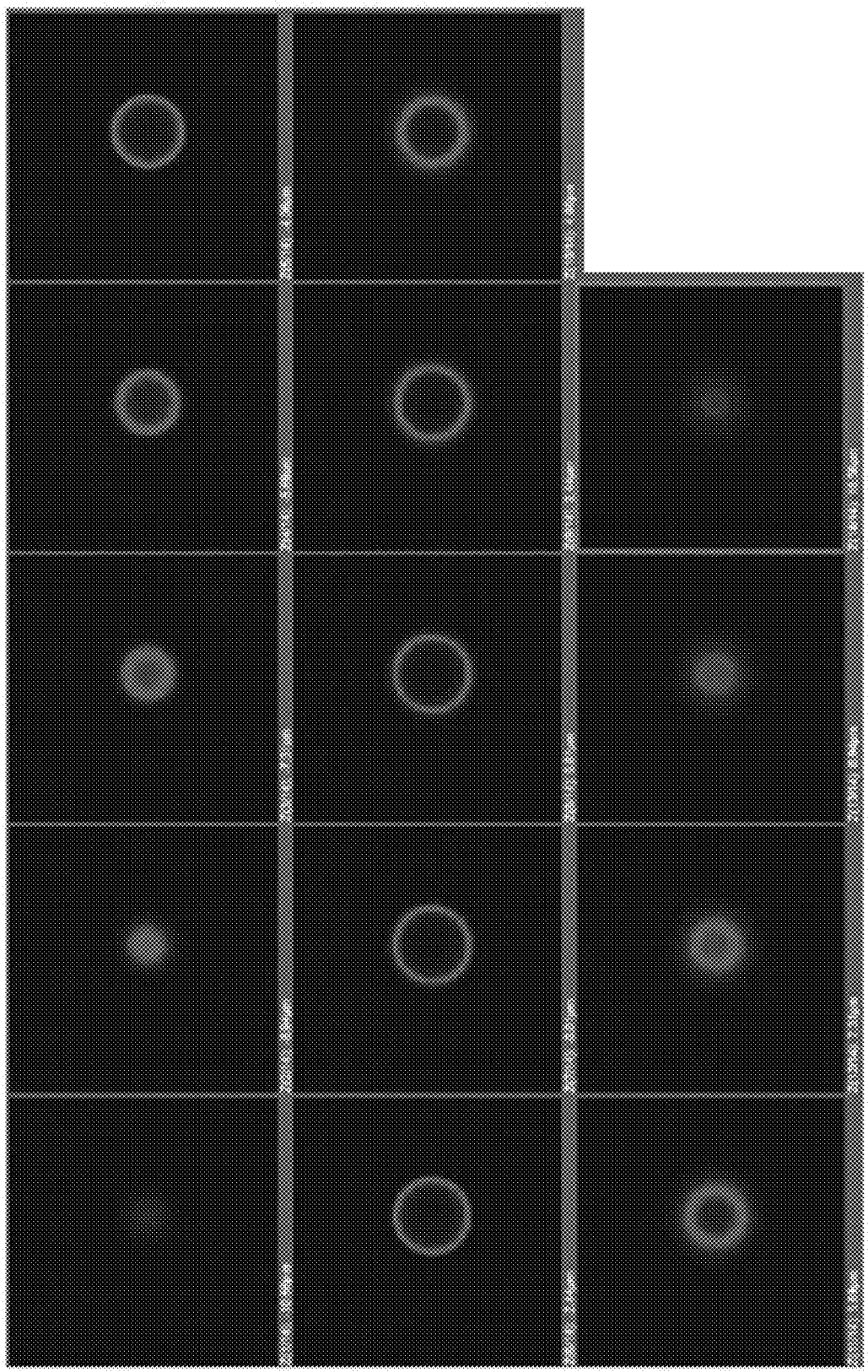

FIGS. 15A-15E illustrate example images of polymer beads, in accordance with various embodiments. The depth of bead shaving can be analyzed using a microscope or other optical system. FIGS. 15A-15E illustrate images of topologically segregated polymer beads labelled with SA AF555 (e.g., 35A beads) used to experimentally assess the shaving depth. FIG. 15A illustrates an image of a topologically segregated polymer bead as imaged using the DAPI channel, FIG. 15B illustrates the topologically segregated polymer bead as imaged using the TRITC channel, and FIG. 15C illustrates the merged channel of the optical system. FIG. 15D illustrates a measurement of the bead shaving depth, which is represented by the difference between the interior and exterior diameters. As illustrated, the exterior diameter is 15.31 microns, the interior diameter is 13.87 microns, and with a difference of 0.72 microns (e.g., 1.44/2). FIG. 15E illustrates a Z-stack of bead cross sections from top to bottom of the topologically segregated polymer bead. In experimental embodiments, the average width of the SA-AF555-biotin signal can be 2.56 microns plus or minus 0.28 microns and the average bead size can be 14.74 microns plus or minus 0.99 microns.

Figure 16A:
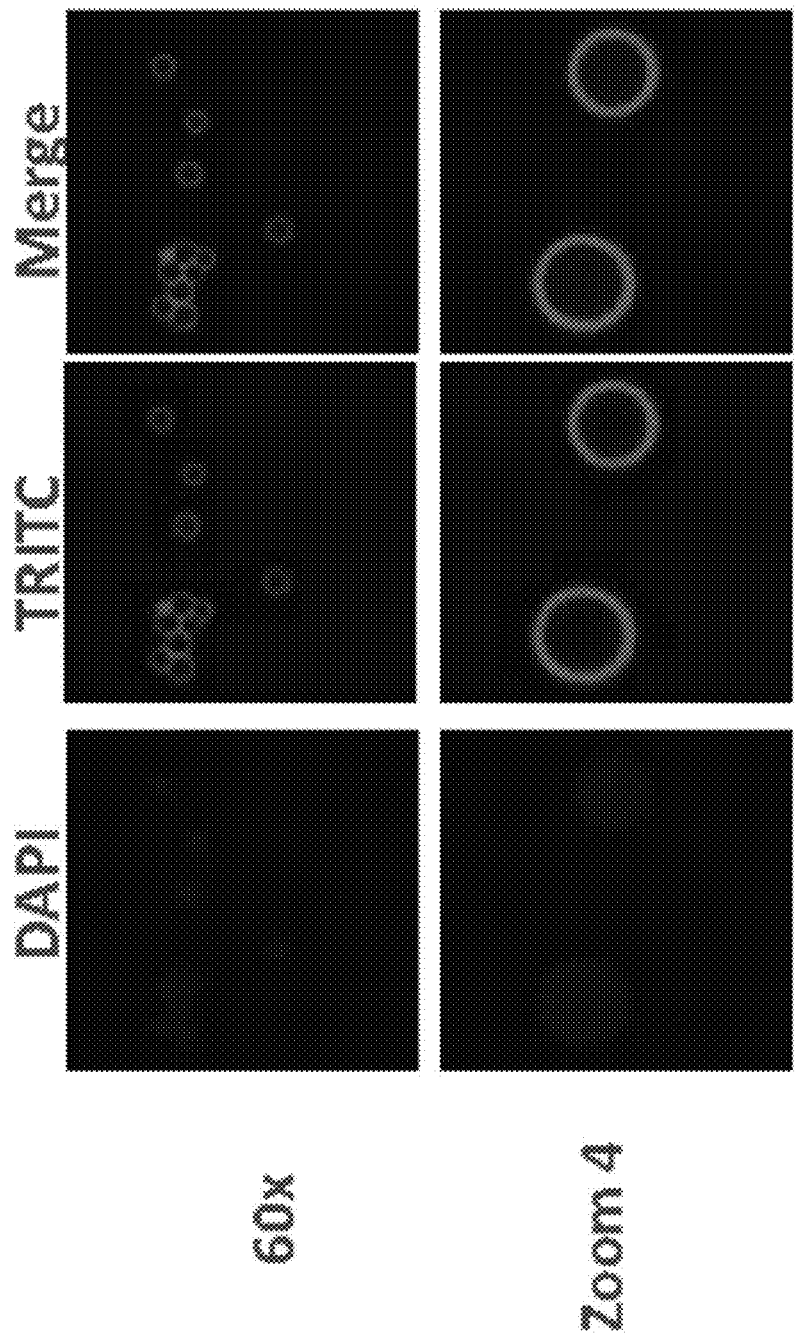
FIGS. 16A-16D illustrate example images of experimentally obtained polymer beads and non-segregated polymer beads, in accordance with various embodiments.
Figure 16B:
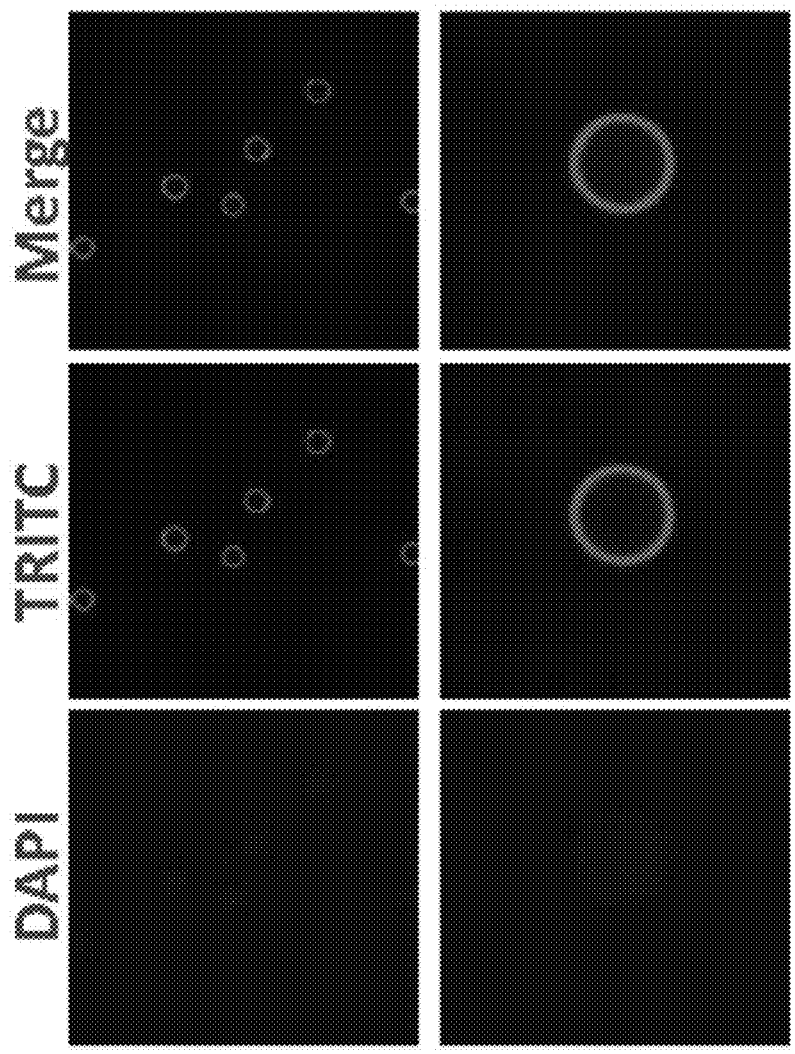
Figure 16D:
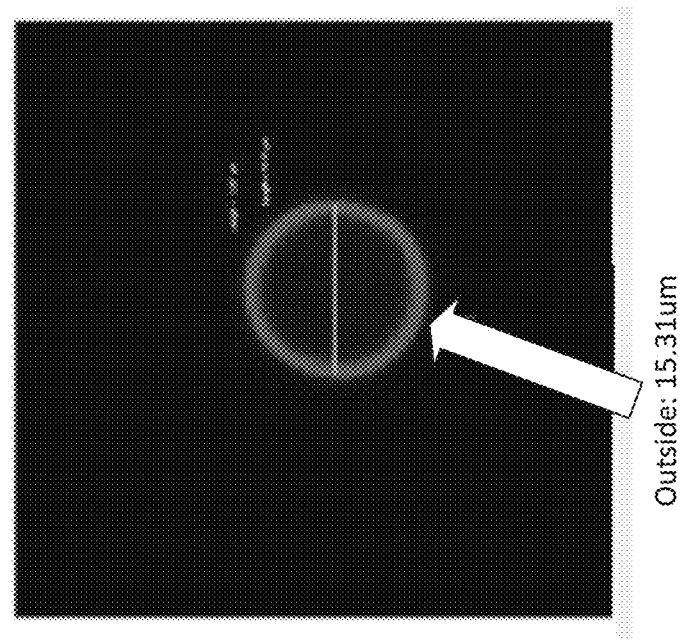
Figure 16C:
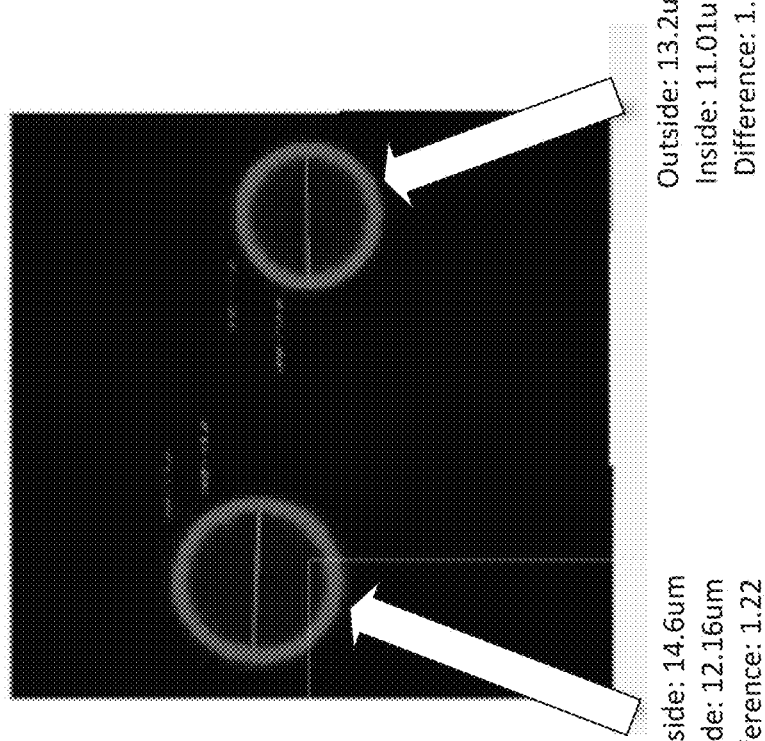

FIGS. 16A-16D illustrate example images of experimentally obtained polymer beads and non-segregated polymer beads, in accordance with various embodiments. The beads are labelled with SA AF555 and imaged using an optical system with multiple channels at 60× and zoom 4. FIG. 16A illustrates images of non-segregated polymer beads labelled with SA AF555 (e.g., 11A beads) and as imaged using the DAPI channel, TRITC channel, and merged channel at both 60× and zoom 4. FIG. 16B illustrates images of topologically segregated polymer beads labelled with SA AF555 (e.g., 35E beads) and as imaged using the DAPI channel, TRITC channel, and merged channel at 60× and zoom 4. FIG. 16C illustrates a measurement of the diameters of non-segregated polymer beads 11A. As illustrated, a first non-segregated polymer bead has an exterior diameter of 14.6 microns, an interior diameter of 12.16 microns, and a difference of 1.22 microns. A second non-segregated polymer bead has an exterior diameter of 13.2 microns, an interior diameter of 11.01 microns, and a difference of 1.1 microns. FIG. 16D illustrates a measurement of the diameters of a topologically segregated polymer bead 35A. As illustrated, the topologically segregated polymer bead has an exterior diameter of 15.31 microns, an interior diameter of 13.87 microns, and a difference of 0.072 microns.

Figure 17A:
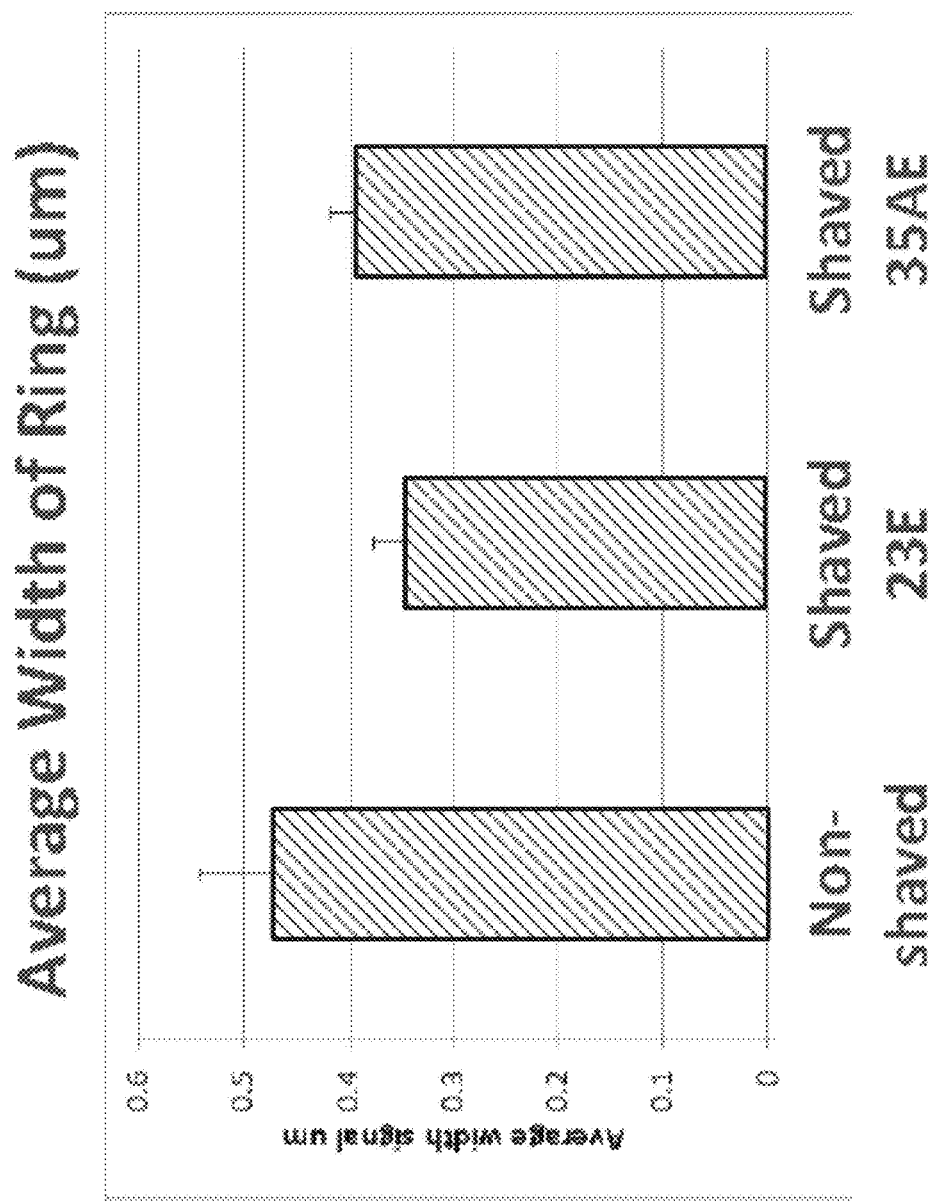
FIGS. 17A-17C illustrate example dimensions of polymer beads, in accordance with various embodiments.
Figure 17B:
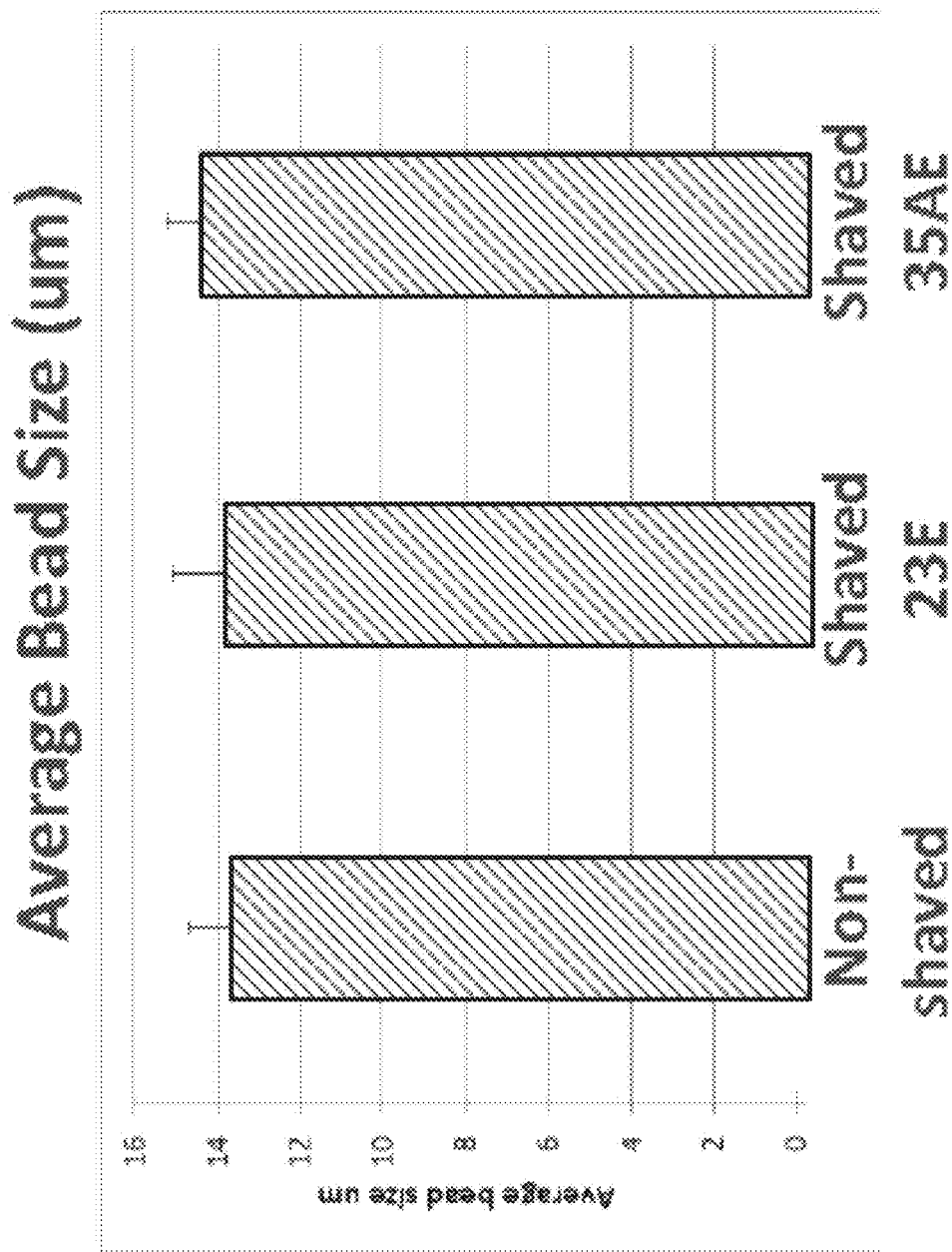
Figure 17C:
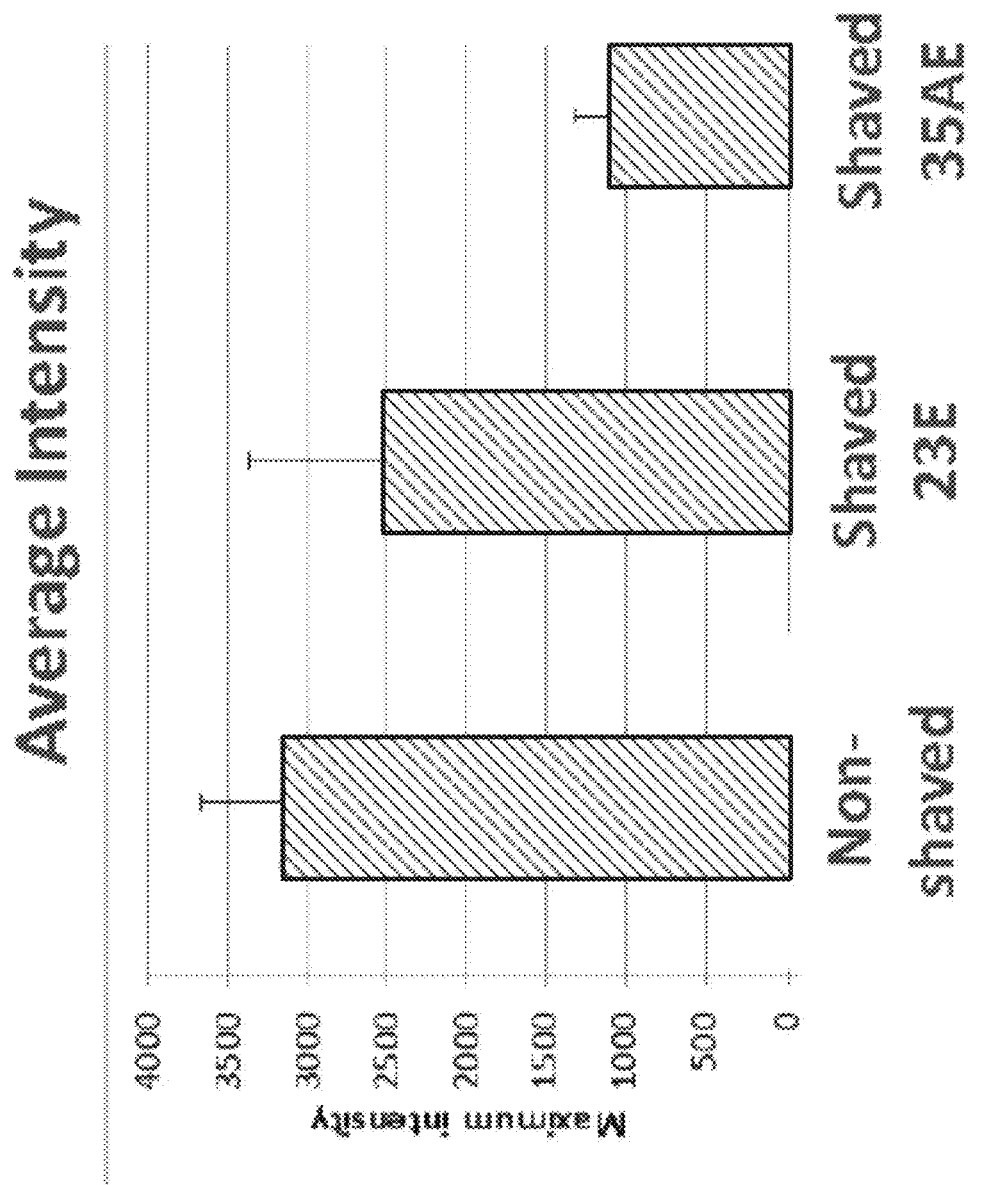

FIGS. 17A-17C illustrate example dimensions of polymer beads, in accordance with various embodiments. FIG. 17A shows example experimental results of the average width of the signal of the ring (e.g., the SA-AF555-biotin signal) for non-segregated polymer beads 11A, topologically segregated polymer beads 23E, and the topologically segregated polymer beads 35A. FIG. 17B shows example experimental results of the average bead size for non-segregated polymer beads 11A, topologically segregated polymer beads 23E, and the topologically segregated polymer beads 35A. FIG. 17C shows example experimental results of the average intensity for non-segregated polymer beads 11A, topologically segregated polymer beads 23E, and the topologically segregated polymer beads 35A.

Figure 18:
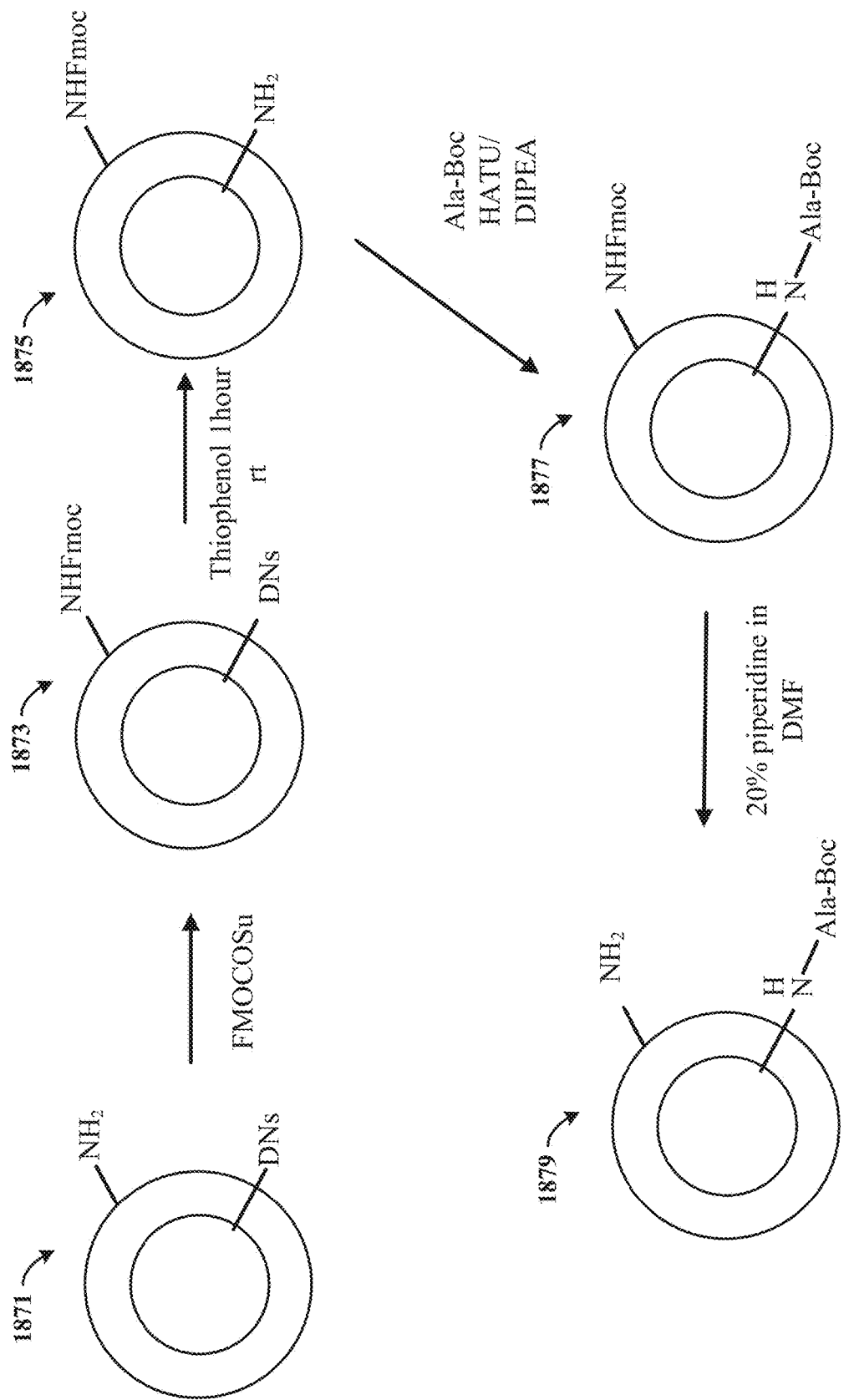
FIG. 18 illustrates an example process for coupling protecting groups on the topologically segregated polymer beads, in accordance with various embodiments.

FIG. 18 illustrates an example process for coupling protecting groups on the polymer beads, in accordance with various embodiments. After forming the topologically segregated beads (e.g., after bead shaving), Fmoc couplings can be used to selectively build polymers on the exterior surface and Boc couplings can be used to selectively build encoding compounds (e.g., barcode peptides) on bead interior surfaces. As illustrated, the topologically segregated bead 1871 is reacted with a solution including Fmoc, such as FmocOSu, resulting in the polymer bead 1873 having exterior surface Fmoc protection and the protecting group, e.g., DNs, in the interior surface. The polymer bead 1873 is reacted with thiophenol (such as for one hour) to remove the protecting group DNs in the interior, resulting the polymer bead 1875. The polymer bead 1875 is reacted with a solution that includes Boc, such as Ala-boc, 1-[Bis(dimethylamino) methylene]-1H-1,2,3-triazolo[4,5-b]pyridinium 3-oxid hexafluorophosphate (HATU)/DIPEA, to couple the free amine group in the interior surface with Boc and resulting in the polymer bead 1877. The Fmoc can be used to selectively build a screening compound via base deprotection followed by coupling chemistry and the Boc in the interior surface can used to selectively build an encoding group (e.g., a barcode peptide) via acid deprotection followed by coupling chemistry. To demonstrate the topological segregation, the polymer bead 1877 having the exterior Fmoc protection and Boc coupling in the interior surface is reacted with a solution including piperidine, such as 20% piperidine in DMF, resulting in the polymer bead 1879 having a free amine group in the exterior surface, which was previously protected by Fmoc.

Figure 19A:
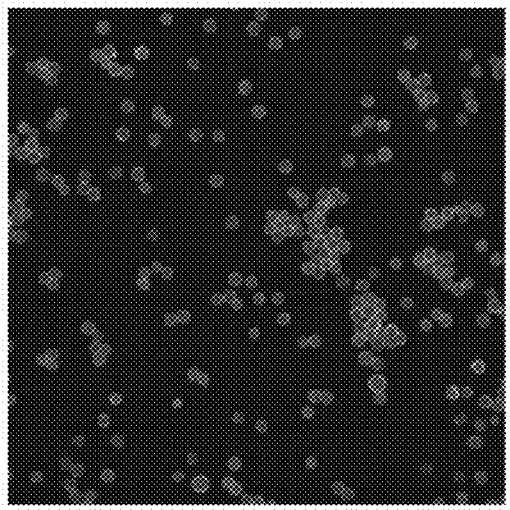
FIGS. 19A-19D illustrate example images of resulting polymer beads formed using the process of FIG. 18, in accordance with various embodiments.
Figure 19B:
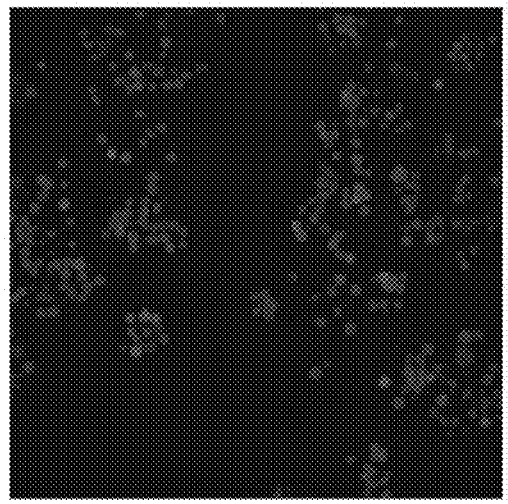
Figure 19C:
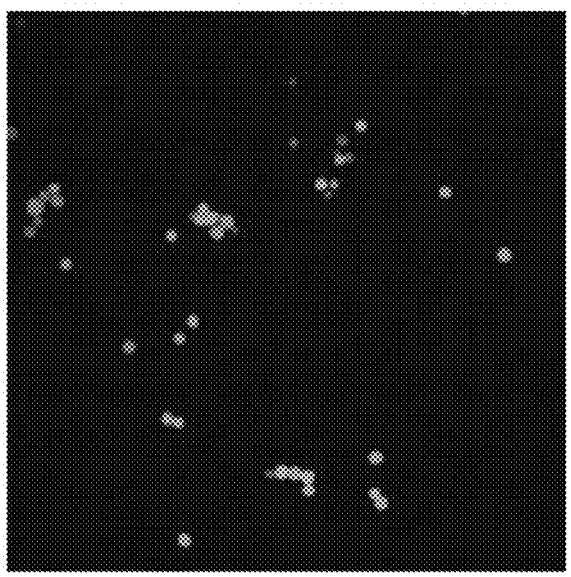
Figure 19D:
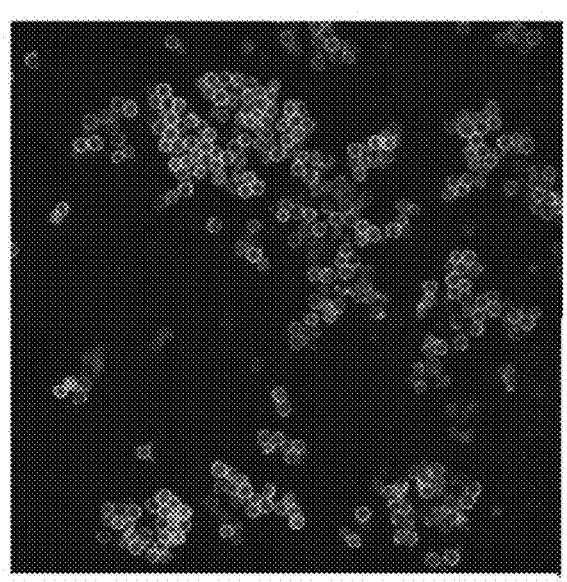

FIG. 19A-19B illustrates example images of resulting polymer beads formed using the process of FIG. 18, in accordance with various embodiments. Specifically, FIG. 19A illustrates an image of the topologically segregated beads 1871, which illustrates the segregation of the exterior surface, having a free amine group (e.g., green), from the interior surface and which has a protecting group and images blue. FIG. 19B illustrates an image of the polymer beads 1873 having exterior surface Fmoc protection and the protecting group in the interior surface, which both image blue caused by autofluorescence of the bead. FIG. 19C illustrates an image of the polymer beads 1875 which illustrates the free amine group in the interior surface (e.g., green). And, FIG. 19D illustrates an image of the polymer bead 1879 which has a free amine group in the exterior surface (e.g., green) and Boc in the interior surface (e.g., blue) and demonstrates that the bead is layered/topologically segregated.

Terms to exemplify orientation, such as in, on, exterior, interior, within, first, second, third, fourth, fifth, etc., may be used herein to refer to relative positions of elements as shown in the figures. It should be understood that the terminology is used for notational convenience only and that in actual use the disclosed structures may be oriented or ordered differently from the orientation or order shown in the figures. For example, a second deprotecting group may be used after a third deprotecting group. Thus, the terms should not be construed in a limiting manner.

Various embodiments are implemented in accordance with the underlying Provisional Application (Ser. No. 62/327,923), entitled "Method for Topological Segregation of Polymer Beads", filed Apr. 26, 2016, to which benefit is claimed and is fully incorporated herein by reference. For instance, embodiments herein and/or in the provisional application (including the appendices therein) may be combined in varying degrees (including wholly). Reference may also be made to the experimental teachings and underlying references provided in the underlying provisional application, each of which are fully incorporated herein for their specific and general teachings related to various compounds, chemical techniques, among other teachings. Embodiments discussed in the Provisional Application are not intended, in any way, to be limiting to the overall technical disclosure, or to any part of the claimed invention unless specifically noted.

Various embodiments described above, and discussed provisional application may be implemented together and/or in other manners. One or more of the items depicted in the present disclosure and in the underlying provisional application can also be implemented separately or in a more integrated manner, or removed and/or rendered as inoperable in certain cases, as is useful in accordance with particular applications. In view of the description herein, those skilled in the art will recognize that many changes may be made thereto without departing from the spirit and scope of the present disclosure.

What is claimed is:
1. A method comprising:
(a) contacting a polymer bead having an interior surface and an exterior surface with a first solution including a nitrobenzenesulfonamide group, resulting in the nitrobenzenesulfonamide group bound directly to a first functional group in the exterior surface and a second functional group in the interior surface, the nitrobenzenesulfonamide group including one of 2-4-Dinitrobenzenesulfonamides (DNs) and 2-nitrobenzenesulfonamide (Ns), wherein the polymer bead is 90 microns or less in size, and wherein the first functional group and the second functional group comprise a plurality of free amine groups;

(b) contacting the polymer bead with a second solution including a protein having free cysteines that selectively deprotects the first functional group in the exterior surface, resulting in a topologically segregated polymer bead including:
  (i) the exterior surface including the first functional group that is deprotected, and
  (ii) the interior surface including the nitrobenzenesulfonamide group bound directly to the second functional group; such that after contacting the polymer bead with the first solution and the second solution;

(c) contacting the polymer bead with a third solution including a second protecting group, resulting in the exterior surface including the second protecting group bound directly to the first functional group and the interior surface including the nitrobenzenesulfonamide group bound directly to the second functional group;

(d) contacting the polymer bead with a fourth solution including thiol, resulting in the exterior surface including the second protecting group bound directly to the first functional group and the interior surface including the second functional group that is deprotected; and (e) contacting the polymer bead with a fifth solution including a third protecting group resulting in the topologically segregated polymer bead having the exterior surface including the second protecting group bound directly to the first functional group and having the interior surface including the third protecting group bound directly to the second functional group, wherein the second protecting group and the third protecting group are different types of groups from one another and provide chemoselectivity for subsequent chemical reactions, and wherein the process results in essentially complete and uniform binding of the second protecting group to the first functional group on the exterior surface of the polymer beads.

2. The method of claim 1, wherein contacting the polymer bead with the first solution, the second solution, the third solution, the fourth solution and the fifth solution includes reacting a plurality of polymer beads, the plurality of polymer beads including the polymer bead, with the first solution, the second solution, the third solution, the fourth solution and the fifth solution, each of the plurality of polymer beads having the interior surface and the exterior surface, and resulting in a plurality of topologically segregated polymer beads that each include the first functional group bound directly to the second protecting group in the exterior surface and the second functional group bound directly to the third protecting group in the interior surface.

3. The method of claim 1, wherein contacting the polymer bead with the second solution includes reacting the polymer bead with the protein having cysteines that selectively deprotects the plurality of free amine groups in exterior surface without deprotecting the plurality of free amine groups in the interior surface, wherein the polymer bead is configured and arranged with pores of a size that the protein having free cysteines does not interact with the nitrobenzenesulfonamide group bound to the second functional group in the interior surface, the first functional group comprising the plurality of free amine groups in the exterior surface amines and the second functional group comprising the plurality of free amine groups in the interior surface.

4. The method of claim 1, wherein the second protecting group and the third protecting group are each selectively deprotected using an acid or a base.

5. The method of claim 1, wherein the second protecting group includes one of fluorenylmethyloxycarbonyl chloride (Fmoc) or tert-butyloxycarbonyl (Boc) and the third protecting group includes the other of Fmoc or Boc, and wherein the second protecting group and the third protecting group are selectively deprotected using an acid and a base.

6. The method of claim 5, further including performing a subsequent chemical reaction including: removing the one of Fmoc or Boc via base or acid decoupling resulting in the first functional group in the exterior surface being deprotected; and coupling the first functional group to a screening compound.

7. The method of claim 5, further including performing a subsequent chemical reaction including: removing the other of the one of Fmoc or Boc via base or acid decoupling resulting in the second functional group in the interior surface being deprotected; and coupling the second functional group to an encoding compound.

8. The method of claim 7, further including: removing the one of Fmoc or Boc via base or acid decoupling resulting in the first functional group in the exterior surface being deprotected; coupling the first functional group to the screening compound; and forming a polymer bead, wherein the exterior surface of the polymer bead is coupled to a screening compound, and the interior surface of the polymer bead is coupled to an encoding compound to provide a topologically segregated polymer bead.

9. The method of claim 1, wherein contacting the polymer bead with the fifth solution results in the topologically segregated polymer bead having the exterior surface including the second protecting group bound directly to the first functional group without a presence of the third protecting group on the exterior surface, and having the interior surface including the third protecting group bound directly to the second functional group.

* * * * *